US007105518B2

(12) United States Patent  
Martin et al.

(10) Patent No.: US 7,105,518 B2  
(45) Date of Patent: Sep. 12, 2006

(54) THIOPYRANE-4-ONES AS DNA PROTEIN KINASE INHIBITORS

(75) Inventors: Niall Morrison Barr Martin, Cambridge (GB); Graeme Cameron Murray Smith, Cambridge (GB); Roger John Griffin, Newcastle Upon Tyne (GB); Bernard Thomas Golding, Newcastle Upon Tyne (JP); Ian Robert Hardcastle, Newcastle Upon Tyne (JP); Laurent Jean Martin Rigoreau, Sussex (GB); David Richard Newell, Newcastle Upon Tyne (GB); Hilary Alan Calvert, Newcastle Upon Tyne (GB); Nicola Jane Curtin, Newcastle Upon Tyne (GB); Paul Workman, Surrey (GB); Florence Irene Raynaud, Surrey (GB); Bernard Paul Nutley, Surrey (GB)

(73) Assignee: Cancer Research Technology Limited, (GB)

( * ) Notice: Subject to any disclaimer, the term of this patent is extended or adjusted under 35 U.S.C. 154(b) by 159 days.

(21) Appl. No.: 10/486,811

(22) PCT Filed: Aug. 14, 2002

(86) PCT No.: PCT/GB02/03740

§ 371 (c)(1),  
(2), (4) Date: Feb. 13, 2004

(87) PCT Pub. No.: WO03/015790

PCT Pub. Date: Feb. 27, 2003

(65) Prior Publication Data

US 2005/0107367 A1    May 19, 2005

(30) Foreign Application Priority Data

Aug. 14, 2001 (GB) .................................. 0119863.9

(51) Int. Cl.  
*A61K 31/382* (2006.01)  
*C07D 335/02* (2006.01)  
*A61N 5/00* (2006.01)  
*A61K 31/5355* (2006.01)  
*C07D 413/04* (2006.01)

(52) U.S. Cl. .................. 514/236.8; 514/432; 544/145; 549/28; 604/20

(58) Field of Classification Search ................ 544/145, 544/28; 604/20; 514/236.8, 432; 549/28  
See application file for complete search history.

(56) References Cited

U.S. PATENT DOCUMENTS

| 4,954,518 | A | 9/1990 | Takano et al. |
|---|---|---|---|
| 5,252,735 | A | 10/1993 | Morris |
| 5,284,856 | A | 2/1994 | Naik et al. |
| 5,302,613 | A | 4/1994 | Morris |
| 5,703,075 | A | 12/1997 | Gammill et al. |
| 5,733,920 | A | 3/1998 | Mansuri et al. |
| 5,922,755 | A | 7/1999 | Tanaka et al. |
| 6,348,311 | B1 | 2/2002 | Kastan et al. |
| 6,387,640 | B1 | 5/2002 | Kastan et al. |
| 2004/0002492 | A1 | 1/2004 | Smith et al. |
| 2004/0023968 | A1 | 2/2004 | Martin et al. |
| 2004/0192687 | A1 | 9/2004 | Martin et al. |

FOREIGN PATENT DOCUMENTS

| EP | 0 610 519 A1 | 8/1994 |
|---|---|---|
| EP | 0 635 268 A1 | 1/1995 |
| EP | 0 640 339 A1 | 3/1995 |
| EP | 0 641 566 A1 | 3/1995 |
| EP | 0 648 492 A2 | 4/1995 |
| EP | 0 658 343 A1 | 6/1995 |
| GB | 1303724 | 1/1973 |
| GB | 2 302 021 A | 1/1997 |
| JP | 03215-423 | 1/1990 |
| WO | WO 90/06921 | 6/1990 |
| WO | WO 91/19707 | 12/1991 |
| WO | WO 92/00290 | 1/1992 |
| WO | WO 95/29673 | 11/1995 |
| WO | WO 96/01108 | 1/1996 |
| WO | WO 97/15658 | 5/1997 |
| WO | WO 97/018323 | 5/1997 |
| WO | WO 98/055602 | 12/1998 |
| WO | WO 98/056391 | 12/1998 |
| WO | WO 99/047494 | 9/1999 |
| WO | WO 01/53266 A1 | 7/2001 |
| WO | WO 02/020500 | 3/2002 |
| WO | WO 02/20500 A2 | 3/2002 |
| WO | WO 02/056912 A2 | 7/2002 |
| WO | WO 03/024949 A1 | 3/2003 |
| WO | WO03/093261 | 4/2003 |
| WO | WO 03/034997 A2 | 5/2003 |
| WO | WO 03/035618 A2 | 5/2003 |
| WO | WO 03/070726 | 8/2003 |

OTHER PUBLICATIONS

Abraham, Robert T., "Cell cycle checkpoint signaling through the ATM and ATR kinases," *Genes & Dev.*, 15:2177-2196 (2001).

Archer, S. et al., "Ring-Hydroxylated Analogues of Lucanthone as Antitumore Agents," *J. Med Chem.*, 25, 220-227 (1982).

Brown, P.O., "Integration of retroviral DNA," *Curr Top Microbiol Immunol.*, 157:19-48 (1990).

Chiosis, G, et al. "LY294002-geldanamycin heterodiamers as selective inhibitors of the P13K and P13k-related family", *Bioorganic & Medicinal Chemistry Letters*, vol. 11, No. 7, Apr. 9 2001 pp. 909-913, XP004232522.

Daniel, Rene, et al., "Wortmannin potentiates integrase-mediated killing of lymphocytes and reduces the efficiency of stable transduction by retroviruses," *Mol. Cell Biol*, 21:4, 1164-1172 (2001).

Durocher, Daniel, and Jackson, Stephen P., "DNA-PK, ATM and ATR as sensors of DNA damage: variations on a theme?," *Curr Opin Cell Biol.*, 13:225-231 (2001).

Giroux, A., et al, "One pot biaryl synthesis *via in situ* boronate formation," *Tet. Lett.*, 38:22, 3841-3844 (1997).

Griffin, et al., "Selective Benzopyranone and Pyrimido [2,1-a]isoquinolin-4-one Inhibitors of DNA-Dependent Protein Kinase: Synthesis, Structure—Activity Studies, and Radiosensitization of a Human Tumor Cell Line in Vitro", *J. Med. Chem.*, 2005, 48, 569-585.

Haselhorst, Dorte, et al., "Development of cell lines stably expressing human immunodeficiency virus type 1 proteins for studies in encapsidation and gene transfer," *J Gen Virol*, 79:231-237 (1998).

Herzog, Karl-Heinz et al., "Requirement for ATM in ionizing radiation-induced cell death in the developing central nervous system," *Science*, 280: 1089-1091 (1998).

Hickson, Ian, et al, "Identification and Characterization of a Novel and Specific Inhibitor of the Ataxia-Telangiectasia Mutated Kinase ATM," *Cancer Research* 64, Dec. 15, 2004, 9152-9159.

Ishiyama, T. et al., "Synthesis of arylboronates via the palladium(0)-catalyzed cross-coupling reaction of tetra(alkoxo)diborons with aryl triflates," *Tell. Lett.*, 38:19, 3447-3450 (1997).

Keith, Curtis T. and Schreiber, Stuart L., "PIK-related kinases: DNA repair, recombination, cell cycle checkpoints," *Science*, 270:50-51 (1995).

Leahy, et al., "Identification of a highly potent and selective DNA-dependent protein kinase (DNA-PK) inhibitor (NU7441) by screening of chromenone librariest," *Bioorganic & Medicinal Chemistry Letters* 14 (2004) 6083-6087.

Metcalfe, Judith A. et al., "Accelerated telomere shortening in ataxia telangiectasia," *Nature Genetics*, 13: 350-353 (1996).

Mlotkowska, B.L. et al., "Two-dimensional NMR studies of 2-substituted thioxanthene sulfoxides," *J. Heterocyclic Chem.*, 28: 731-736 (Apr.-May 1991).

Naldini, Luigi et al., "In vivo gene delivery and stable transduction of nondividing cells by a lentiviral vector," *Science*, 272: 263-267 (1996).

Sarkaria, Jann N. et al., "Inhibition of ATM and ATR kinase activities by the radiosensitizing agent, caffeine," *Cancer Res.*, 59: 4375-4382 (1999).

Savitsky, Kinneret et al., "A single ataxia telangiectasia gene with a product similar to P1-3 kinase," *Science*, 268:1749-1753 (1995).

Shiloh, Yosef,"ATM and ATR: networking cellular responses to DNA damage," *Curr. Opin. Genet. Dev.*, 11:71-77 (2001).

Willmore, et al., "A novel DNA-dependent protein kinase inhibitor, NU7026, potentiates the cytotoxicity of topoisomerase II poisons used in the treatment of leukemia", *Blood*, Jun. 15, 2004, vol. 103, No. 12, 4659-4665.

Zakian, Virginia A., "ATM-related genes: What do they tell us about functions of the human gene?" *Cell*, 82:685-687 (1995).

Banin, S., et al, "Enhanced phosphorylation of p53 ATM in response to DNA damage," *Science*, 1998, vol. 281, pp. 1674-1677.

Bantick, J.R., et al., "Synthesis of 2-aminochromones," *J. Heterocyclic Chem.*, 1981, vol. 18, pp. 679-684.

Berge, et al., "Pharmaceutically acceptable salts," *J. Pharm. Sci.*, 1977, vol. 66, pp. 1-19.

Bettoni, et al., "Synthesis and absolute configuration of substituted morpholines," *Tetrahedron*, 1980, vol. 36, pp. 409-415.

Boyd, J., et al., "The chemistry of the 'insoluble red' woods," *J. Chem. Soc.*, 1948, pp. 174-176.

Buon, C., et al., "Synthesis of 3-substituted and 2,3-disubstituted-4H-1,4- Benzoxazines," *Tetrahedron*, 2000, vol. 56, pp. 605-614.

Daniel, R., et al., "A role for DNA-PK in retroviral DNA integration," *Science*, 1999, vol. 284, pp. 644-647.

Datta, A., et al., "Reformatsky reaction on aroylketene S, N-acetals: a facile route to 4-amino-6-aryl-2H-pyran-2-ones," *Synthesis*, 1988, vol. 3, pp. 248-250.

Di Braccio, M., et al., "1,2-fused pyrimidines VII," *Eur. J. Med., Chem.*, 1995, vol. 30, No. 1, pp. 27-38.

Di Braccio, M., et al., "Pyran derivatives XIX. (Dialkylamino) substituted 1-benzopyranones and naphthopyranoes with platelet antiaggregating activity," *Farmaco*, 1995, vol. 50, No. 10, pp. 703-711.

Ermili, A., et al., "Chemical and pharmacological research on pyran derivatives," Enclosed: *Chemical Abstracts*, 1977, vol. 87, No. 15, p. 588 (XP-002218602). 117750g.

Gell, D., et al., "Mapping of protein-protein interactions within the DNA-dependent protein kinase complex," *Nucleic Acid Res.*, 1999, vol. 27, No. 17, pp. 3494-3502.

Goytisolo, et al., "The absence of DNA-dependent protein kinase catalytic subunit in mice results in anaphase bridges and in increased telomeric fusions with normal telomere length and G-strand overhang," *Mol. Cell. Biol.*, 2001, vol. 21, No. 11, pp. 3642-3651.

Green, T., et al., *Protective groups in organic synthesis*, 1999, Wiley.

Hartley, K. O., et al., "DNA-dependent protein kinase catalytic subunit: a relative of phosphatidylinositol 3-kinase and the ataxia telengiectasia gene product," *Cell*, vol. 82, pp. 849-856.

Hollick, J. J., et al., "2,6-disubstituted pyran-4-one and thiopyran-4-one inhibitors of DNA-dependent protein kinase (DNA-PK)," *Bioorganic & Medicinal Chemistry Letters*, 2003, vol. 13, pp. 3083-3086.

Izzard, R.A., et al., "Competitive & noncompetitive inhibition of the DNA-dependent protein kinase," *Cancer Research*, 1999, vol. 59, No. 11, pp. 2581-2586.

Jackson, S. P., "DNA damage detection by DNA dependent protein kinase and related enzymes," *Cancer Surv.*, 1996, vol. 28, pp. 261-279.

Jung, J. C., et al., "Simple and cost effective synthesis of 4-hydroxycoumarin," *Synth. Commun.*, 1999, vol. 29, No. 20, pp. 3587-3595.

Knight, A.R., et al., "Isolation and characterization of 4-chloro-3,4'; 3',4"-tercoumarin, *Can. J. Chem.*, 1968, vol. 46, pp. 2495-2499.

Kubik, et al., "Fine tuning of the cation affinity of artificial receptors based on cyclic peptides by intramolecular conformational control," *Eur. J. Org. Chem.*, 2001, pp. 311-312.

Lavin, M. F., et al., "The genetic defect in ataxia-telangiectasia," *Annu. Rev. Immunol.*, 1997, vol. 15, pp. 177-202.

Morris, J., et al., "Synthesis and biological evaluation of antiplatelet 2-aminochromones," *J. Med. Chem.*, 1993, vol. 36, No. 14, pp. 2026-2032.

Morris, J., et al., "Synthesis of 2-amino-6-phenyl-4H-pyran-4-ones," *Synthesis*, 1994, pp. 43-46.

Morris, J., et al., "Reaction of phosgeniminium salts with enolates derived from Lewis acid complexes of 2'-hydroxypropiophenones and related β-Diketones," *J. Org. Chem.*, 1996, vol. 61, No. 9, pp. 3218-3220.

Oh, C., et al., "Nucleophilic vinylic substitution of halocoumarins and halo-1,4-napthoquinones with morpholine," *J. Heterocyclic Chem.*, 1994, vol. 31, pp. 841-843.

*Remington's Pharmaceutical Sciences*, 1990, 18 Ed., Mack Publish. Co., Easton.

Roma, G., et al., "Synthesis, antiplatelet activity and comparative molecular field analysis of substituted 2-amino-4H pyrido[1,2-a]pyrimidin-4-ones, their congeners and isosteric analogues," *Bioorganic & Medicinal Chemistry*, 2000, vol. 8, pp. 751-768.

Roma, G., et al., "Pyran derivatives XX. 2-aminochromone benzo-fused derivatives with antiproliferative properties," *II Farmaco*, 1998, vol. 53, pp. 494-503.

Rosenzweig, K.E., et al., "Radiosensitization of human tumor cells by the phosphatidylinositol 3-kinase inhibitors Wortmannin and LY294002 correlates with inhibition of DNA-dependent protein kinase and prolonged G2-M delay," *Clin. Cancer Res.*, 1999, vol. 3, 1149-1156.

Schroth, W., et al., "2,4,6-Tris(dialkylamino) pyrylium salts and related systems, synthesis and reaction behavior," *Tetrahedron Letters*, 1988, vol. 29, No. 37, pp. 4695-4698.

Schroth, W. et al., "2,4,6-Tris(dialkylamino) pyrylium salts and related systems, synthesis and reaction behavior," *Chemical Abstracts*, 110:135031.

Skehan, P., et al., "New colorimetric cytotoxicity assay for anticancer-drug screening," *J. Natl. Cancer Inst.*, 1990, vol. 82, No. 13, pp. 1107-1112.

Smith, G. C. M., et al., "The DNA-dependent protein kinase," *Genes & Dev.*, 1999, vol. 13, pp. 916-934.

Synder, et al., "Structure and reactions of malonyl-α-aminopyridine. I," *J. Am. Chem. Soc.*, 1952, vol. 74, pp. 4910-4914.

Ten Hoeve, et al., "Direct substitution of aromatic ethers by lithium amides. A new aromatic amination reaction," *J. Org. Chem.*, 1993, vol. 58, pp. 5101-5106.

Toker, A., et al., "Signaling through the lipid products of phosphinositide-3-OH kinase," *Nature*, 1997, vol. 387, pp. 673-676.

Veuger, S. J., et al., "Radiosensitization and DNA repair inhibition by the combined use of novel inhibitors of DNA-dependent protein kinase and poly (ADP-ribose) polymerase-1," *Cancer Research*, 2003, vol. 63, pp. 6008-6015.

Vlahos, C. J., et al., "A specific inhibitor of phosphatidylinositol 3-kinase, 2-(4- morpholinyl)-8-phenyl-4H-1-benzopyran-4-one (LY294002)," *J. Biol. Chem.*, 1994, vol. 269, No. 7, pp. 5241-5248.

Wymann, M. T., et al., "Wortmannin inactivates phosphoinositide-3-kinase by covalent modification of Lys-802, a residue involved in the phosphate transfer reaction," *Mol. Cell Biol.*, 1996, vol. 16, No. 4, pp. 1722-1733.

Ismail, I.H. et al., "SUI1752 inhibits the DNA-dependent protein kinase and DNA double-strand break repair resulting in ionizing radiation sensitization," Oncogene (2004) 23:873-883.

Kashishian, A. et al., "DNA-dependent protein kinase inhibitors as drug candidates for the treatment of cancer," Mol. Cancer Ther. (2003) 2:1257-1264.

Lau et al., "Suppression of HIV-1 infection by a small molecule inhibitor of the ATM kinase," Nature cell Biology (2005) 7:493-500.

Muller, C. et al., "DNA-dependent protein kinase activity correlates with clinical and in vitro sensitivity of chronic lymphocytic leukemia lymphocytes to nitrogen mustards," Blood (1998) 92:2213-2219.

Sirzen, F. et al., "DNA-dependent protein kinase content and activity in lung carcinoma cell lines: Correlation with intrinsic radiosensitivity," Eur. J. Cancer (1999) 35:111-116.

*Primary Examiner*—Bernard Dentz
(74) *Attorney, Agent, or Firm*—Michael Best & Friedrich LLP

(57) ABSTRACT

The present invention provides compounds of formula (I) and isomers, salts, solvates, chemically protected forms, and prodrugs thereof, wherein $R^1$ and $R^2$ are independently hydrogen, an option ally substituted $C_{1-7}$ alkyl group, $C_{3-20}$ heterocyclyl group, or $C_{5-20}$ aryl group, or may together form, along with the nitrogen atom to which they are attached, an optionally substituted heterocyclic ring having from 4 to 8 ring atoms; and $R^3$ is an optionally substituted $C_{3-20}$ heterocyclyl or $C_{5-20}$ aryl group, and their use as pharmaceuticals, particularly in treating diseases which are retroviral mediated or ameliorated by the inhibition of DNA-PK,

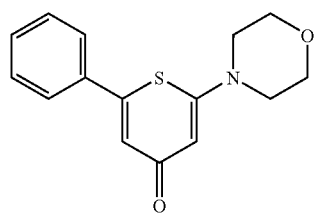

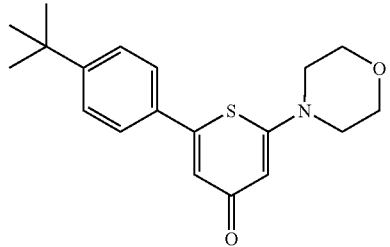

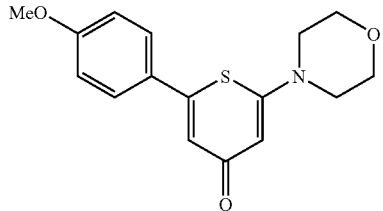

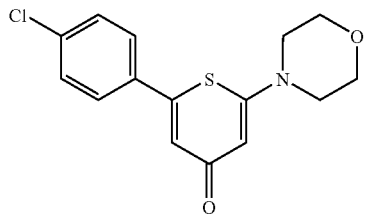

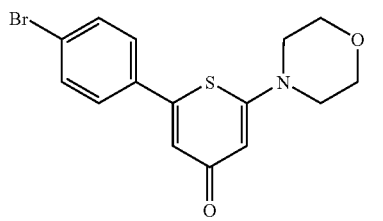

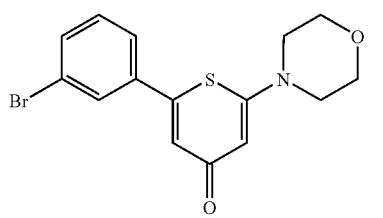

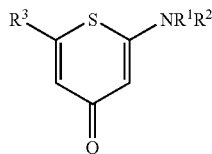

8 Claims, 1 Drawing Sheet

THIOPYRANE-4-ONES AS DNA PROTEIN KINASE INHIBITORS

This application is a national stage entry of PCT/GB02/03740 filed Aug. 14, 2002.

The present invention relates to compounds which act as DNA-PK inhibitors, their use and synthesis.

The DNA-dependent protein kinase (DNA-PK) is a nuclear serine/threonine protein kinase that is activated upon association with DNA. Biochemical and genetic data have revealed this kinase to be composed of a large catalytic subunit, termed DNA-PKcs, and a regulatory component termed Ku. DNA-PK has been shown to be a crucial component of both the DNA double-strand break (DSB) repair machinery and the V(D)J recombination apparatus. In addition, recent work has implicated DNA-PK components in a variety of other processes, including the modulation of chromatin structure and telomere maintenance (Smith, G. C. M. and Jackson, S. P., Genes and Dev. 13: 916–934 (1999)).

Human DNA is constantly under attack from reactive oxygen intermediates principally from by-products of the oxidative metabolism we have evolved for energy supply. Reactive oxygen species are capable of producing DNA single-strand breaks and, where two of these are generated in close proximity, DNA double strand breaks (DSBs). In addition, single- and double-strand breaks can be induced when a DNA replication fork encounters a damaged template, and are generated by exogenous agents such as ionising radiation (IR) and certain anti-cancer drugs (e.g. bleomycin). DSBs also occur as intermediates in site-specific V(D)J recombination, a process that is critical for the generation of a functional vertebrate immune system. If DNA DSBs are left unrepaired or are repaired inaccurately, mutations and/or chromosomal aberrations are induced, which in turn may lead to cell death. To combat the serious threats posed by DNA DSBS, eukaryotic cells have evolved several mechanisms to mediate their repair. In higher eukaryotes, the predominant of these mechanisms is DNA non-homologous end-joining (NHEJ), also known as illegitimate recombination. DNA-PK plays a key role in this pathway.

Biochemical studies on DNA-PK revealed that it is activated most potently by DNA DSBs, suggesting that it might play a role in recognising DNA damage. This stimulated investigations into the potential role of DNA-PKcs and Ku in DNA repair and led to the identification of cell lines which are radiosensitive due to mutations in DNA-PK components (Smith and Jackson, 1999). Cloning of the DNA-PKcs cDNA revealed that it corresponds to a ~470 kDa polypeptide, the N-terminal ~3500 amino acid residues of which does not appear to have significant homology to other characterised proteins (Hartley, K. O., et al., Cell 82: 849–856 (1995)). More significantly, the C-terminal ~500 amino acid residues of DNA-PKcs comprises a catalytic domain that falls into the PI 3-kinase family. Although this initially suggested that DNA-PK might be capable of phosphorylating inositol phospho-lipids, like certain well-characterised members of the PI 3-kinase family (Toker, A. and Cantley, L. C., Nature 387: 673–676 (1997)), the available evidence indicates that DNA-PK has protein but not lipid kinase activity (Hartley et al. 1995; Smith et al., 1999). At a similar time to the cloning of the DNA-PKcs cDNA, the genes and cDNAs for a range of other large PI 3-kinase like (PIKL) proteins were identified and cloned (Jackson, S. P., Cancer Surv. 28: 261–279 (1996)). These proteins have been shown to be involved in controlling transcription, the cell-cycle and/or genome stability in organisms from yeast to man. DNA-PKcs appears to be restricted to higher eukaryotes.

Besides DNA-PKcs, probably the best characterised member of the PIKL family is ATM, the protein deficient in the human neurodegenerative and cancer predisposition condition ataxia-telangiectasia (A-T; Lavin, M. F. and Shiloh,Y., Annu. Rev. Immunol. 15: 177–202 (1997)). ATM has been linked intimately to the detection and signalling of DNA damage.

It has been previously found that the PI 3-kinase inhibitor LY294002:

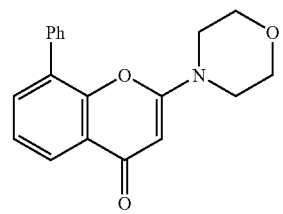

is also able to inhibit DNA-PK function in vitro (Izzard, R. A., et al., Cancer Res. 59: 2581–2586 (1999)). The $IC_{50}$ (concentration at which 50% of enzyme activity is lost) for LY294002 towards DNA-PK is, at ~1 µM, the same as that for PI 3-kinase. Furthermore it has been shown that LY294002 is also able to weakly sensitise cells to the effects of IR (Rosenzweig, K. E., et al., Clin. Cancer Res. 3: 1149–1156 (1999)).

Given the involvement of DNA-PK in DNA repair processes, and that LY294002 has been shown to radiosensitise mammalian cells in culture, an application of (specific) DNA-PK inhibitory drugs would be to act as agents that will enhance the efficacy of both cancer chemotherapy and radiotherapy. DNA-PK inhibitors may also prove useful in the treatment of retroviral mediated diseases. For example it has been demonstrated that loss of DNA-PK activity severely represses the process of retroviral integration (Daniel R, et al., Science, 284:644–7 (1999)). DNA-PK inhibitors may also have potential as modulators of the immune system. DNA-PK has also been shown to play an important role in telomere maintenance, and hence inhibitors of DNA-PK may play a role in modulating telomere functions (Goytisolo, et al., Mol. Cell. Biol., 21:3642–3651 (2001).

The present inventors have now discovered a new class of compounds which exhibit inhibition of DNA-PK; these compounds also exhibit selective inhibition of DNA-PK over the PI 3-kinase family members PI 3-kinase and ATM.

Accordingly, the first aspect of the invention provides for compounds of formula I:

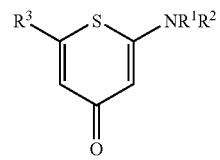

and isomers, salts, solvates, chemically protected forms, and prodrugs thereof, wherein:

$R^1$ and $R^2$ are independently hydrogen, an optionally substituted $C_{1-7}$ alkyl group, $C_{3-20}$ heterocyclyl group, or $C_{5-20}$ aryl group, or may together form, along with the nitrogen atom to which they are attached, an optionally substituted heterocyclic ring having from 4 to 8 ring atoms; and $R^3$ is an optionally substituted $C_{3-20}$ heterocycyl or $C_{5-20}$ aryl group.

A second aspect of the invention provides for the use of compounds of formula I:

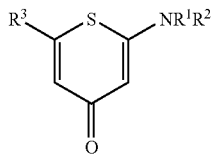

and isomers, salts, solvates, chemically protected forms, and prodrugs thereof, in the preparation of a medicament for inhibiting the activity of DNA-PK, wherein:

$R^1$ and $R^2$ are independently hydrogen, an optionally substituted $C_{1-7}$ alkyl group, $C_{3-20}$ heterocyclyl group, or $C_{5-20}$ aryl group, or may together form, along with the nitrogen atom to which they are attached, an optionally substituted heterocyclic ring having from 4 to 8 ring atoms; and $R^3$ is an optionally substituted $C_{3-20}$ heterocyclyl or $C_{5-20}$ aryl group.

It is preferred that the medicament of the second aspect selectivity inhibits the activity of DNA-PK compared to PI 3-kinase and/or ATM. Selectivity is an important issue as inhibition of other PI 3-kinase family members may lead to unwanted side-effects associated with the loss of function of those enzymes.

A third aspect of the invention provides for the use of compounds as defined in the first aspect of the invention in the preparation of a medicament for use as an adjunct in cancer therapy or for potentiating tumour cells for treatment with ionising radiation or chemotherapeutic agents.

A fourth aspect of the invention provides for the use of compounds in the preparation of a medicament for the treatment of retroviral mediated diseases or disease ameliorated by the inhibition of DNA-PK.

A further aspect of the invention provides an active compound as described herein for use in a method of treatment of the human or animal body, preferably in the form of a pharmaceutical composition.

Another aspect of the invention provides a method of inhibiting DNA-PK in vitro or in vivo, comprising contacting a cell with an effective amount of an active compound as described herein.

Definitions $C_{1-7}$ alkyl: The term "$C_{1-7}$ alkyl", as used herein, pertains to a monovalent moiety obtained by removing a hydrogen atom from a $C_{1-7}$ hydrocarbon compound having from 1 to 7 carbon atoms, which may be aliphatic or alicyclic, or a combination thereof, and which may be saturated, partially unsaturated, or fully unsaturated.

Examples of saturated linear $C_{1-7}$ alkyl groups include, but are not limited to, methyl, ethyl, n-propyl, n-butyl, and n-pentyl (amyl).

Examples of saturated branched $C_{1-7}$ alkyl groups include, but are not limited to, iso-propyl, iso-butyl, sec-butyl, tert-butyl, and neo-pentyl.

Examples of saturated alicyclic $C_{1-7}$ alkyl groups (also referred to as "$C_{3-7}$ cycloalkyl" groups) include, but are not limited to, groups such as cyclopropyl, cyclobutyl, cyclopentyl, and cyclohexyl, as well as substituted groups (e.g., groups which comprise such groups), such as methylcyclopropyl, dimethylcyclopropyl, methylcyclobutyl, dimethylcyclobutyl, methylcyclopentyl, dimethylcyclopentyl, methylcyclohexyl, dimethylcyclohexyl, cyclopropylmethyl and cyclohexylmethyl.

Examples of unsaturated $C_{1-7}$ alkyl groups which have one or more carbon-carbon double bonds (also referred to as "$C_{2-7}$alkenyl" groups) include, but are not limited to, ethenyl (vinyl, —CH=CH$_2$), 2-propenyl (allyl, —CH—CH=CH$_2$), isopropenyl (—C(CH$_3$)=CH$_2$), butenyl, pentenyl, and hexenyl.

Examples of unsaturated $C_{1-7}$ alkyl groups which have one or more carbon-carbon triple bonds (also referred to as "$C_{2-7}$ alkynyl" groups) include, but are not limited to, ethynyl (ethinyl) and 2-propynyl (propargyl).

Examples of unsaturated alicyclic (carbocyclic) $C_{1-7}$ alkyl groups which have one or more carbon-carbon double bonds (also referred to as "$C_{3-7}$cycloalkenyl" groups) include, but are not limited to, unsubstituted groups such as cyclopropenyl, cyclobutenyl, cyclopentenyl, and cyclohexenyl, as well as substituted groups (e.g., groups which comprise such groups) such as cyclopropenylmethyl and cyclohexenylmethyl.

$C_{3-20}$ heterocyclyl: The term "$C_{3-20}$ heterocyclyl," as used herein, pertains to a monovalent moiety obtained by removing a hydrogen atom from a ring atom of a $C_{3-20}$ heterocyclic compound, said compound having one ring, or two or more rings (e.g., spiro, fused, bridged), and having from 3 to 20 ring atoms, atoms, of which from 1 to 10 are ring heteroatoms, and wherein at least one of said ring(s) is a heterocyclic ring. Preferably, each ring has from 3 to 7 ring atoms, of which from 1 to 4 are ring heteroatoms. "$C_{3-20}$" denotes ring atoms, whether carbon atoms or heteroatoms.

Examples of $C_{3-20}$ heterocyclyl groups having one nitrogen ring atom include, but are not limited to, those derived from aziridine, azetidine, pyrrolidines (tetrahydropyrrole), pyrroline (e.g., 3-pyrroline, 2,5-dihydropyrrole), 2H-pyrrole or 3H-pyrrole (isopyrrole, isoazole), piperidine, dihydropyridine, tetrahydropyridine, and azepine.

Examples of $C_{3-20}$ heterocyclyl groups having one oxygen ring atom include, but are not limited to, those derived from oxirane, oxetane, oxolane (tetrahydrofuran), oxole (dihydrofuran), oxane (tetrahydropyran), dihydropyran, pyran ($C_6$), and oxepin. Examples of substituted $C_{3-20}$ heterocyclyl groups include sugars, in cyclic form, for example, furanoses and pyranoses, including, for example, ribose, lyxose, xylose, galactose, sucrose, fructose, and arabinose.

Examples of $C_{3-20}$ heterocyclyl groups having one sulphur ring atom include, but are not limited to, those derived from thiirane, thietane, thiolane (tetrahydrothiophene), thiane (tetrahydrothiopyran), and thiepane.

Examples of $C_{3-20}$ heterocyclyl groups having two oxygen ring atoms include, but are not limited to, those derived from dioxolane, dioxane, and dioxepane.

Examples of $C_{3-20}$ heterocyclyl groups having two nitrogen ring atoms include, but are not limited to, those derived from imidazolidine, pyrazolidine (diazolidine), imidazoline, pyrazoline (dihydropyrazole), and piperazine.

Examples of $C_{3-20}$ heterocyclyl groups having one nitrogen ring atom and one oxygen ring atom include, but are not limited to, those derived from tetrahydrooxazole, dihydrooxazole, tetrahydroisoxazole, dihydroisoxazole, morpholine, tetrahydrooxazine, dihydrooxazine, and oxazine.

Examples of $C_{3-20}$ heterocyclyl groups having one oxygen ring atom and one sulphur ring atom include, but are not limited to, those derived from oxathiolane and oxathiane (thioxane).

Examples of $C_{3-20}$ heterocyclyl groups having one nitrogen ring atom and one sulphur ring atom include, but are not limited to, those derived from thiazoline, thiazolidine, and thiomorpholine.

Other examples of $C_{3-20}$ heterocyclyl groups include, but are not limited to, oxadiazine and oxathiazine.

Examples of heterocyclyl groups which additionally bear one or more oxo (=O) groups, include, but are not limited to, those derived from:

$C_5$ heterocyclics, such as furanone, pyrone, pyrrolidone (pyrrolidinone), pyrazolone (pyrazolinone), imidazolidone, thiazolone, and isothiazolone;

$C_6$ heterocyclics, such as piperidinone (piperidone), piperidinedione, piperazinone, piperazinedione, pyridazinone, and pyrimidinone (e.g., cytosine, thymine, uracil), and barbituric acid;

fused heterocyclics, such as oxindole, purinone (e.g., guanine), benzoxazolinone, benzopyrone (e.g., coumarin);

cyclic anhydrides (—C(=O)—O—C(=O)— in a ring), including but not limited to maleic anhydride, succinic anhydride, and glutaric anhydride;

cyclic carbonates (—O—C(=O)—O— in a ring), such as ethylene carbonate and 1,2-propylene carbonate;

imides (—C(=O)—NR—C(=O)— in a ring), including but not limited to, succinimide, maleimide, phthalimide, and glutarimide;

lactones (cyclic esters, —O—C(=O)— in a ring), including, but not limited to, β-propiolactone, γ-butyrolactone, δ-valerolactone (2-piperidone), and ε-caprolactone;

lactams (cyclic amides, —NR—C(=O)— in a ring), including, but not limited to, β-propiolactam, γ-butyrolactam (2-pyrrolidone), δ-valerolactam, and ε-caprolactam;

cyclic carbamates (—O—C(=O)—NR— in a ring), such as 2-oxazolidone;

cyclic ureas (—NR—C(=O)—NR— in a ring), such as 2-imidazolidone and pyrimidine-2,4-dione (e.g., thymine, uracil).

$C_{5-20}$ aryl: The term "$C_{5-20}$ aryl", as used herein, pertains to a monovalent moiety obtained by removing a hydrogen atom from an aromatic ring atom of a $C_{5-20}$ aromatic compound, said compound having one ring, or two or more rings (e.g., fused), and having from 5 to 20 ring atoms, and wherein at least one of said ring(s) is an aromatic ring. Preferably, each ring has from 5 to 7 ring atoms.

The ring atoms may be all carbon atoms, as in "carboaryl groups", in which case the group may conveniently be referred to as a "$C_{5-20}$ carboaryl" group.

Examples of $C_{5-20}$ aryl groups which do not have ring heteroatoms (i.e. $C_{5-20}$ carboaryl groups) include, but are not limited to, those derived from benzene (i.e. phenyl) ($C_6$), naphthalene ($C_{10}$), anthracene ($C_{14}$), phenanthrene ($C_{14}$), naphthacene ($C_{18}$), and pyrene ($C_{16}$)

Examples of aryl groups which comprise fused rings, one of which is not an aromatic ring, include, but are not limited to, groups derived from indene and fluorene.

Alternatively, the ring atoms may include one or more heteroatoms, including but not limited to oxygen, nitrogen, and sulphur, as in "heteroaryl groups". In this case, the group may conveniently be referred to as a "$C_{5-20}$ heteroaryl" group, wherein "$C_{5-20}$" denotes ring atoms, whether carbon atoms or heteroatoms. Preferably, each ring has from 5 to 7 ring atoms, of which from 0 to 4 are ring heteroatoms.

Examples of $C_{5-20}$ heteroaryl groups include, but are not limited to, $C_5$ heteroaryl groups derived from furan (oxole), thiophene (thiole), pyrrole (azole), imidazole (1,3-diazole), pyrazole (1,2-diazole), triazole, oxazole, isoxazole, thiazole, isothiazole, oxadiazole, and oxatriazole; and $C_6$ heteroaryl groups derived from isoxazine, pyridine (azine), pyridazine (1,2-diazine), pyrimidine (1,3-diazine; e.g., cytosine, thymine, uracil), pyrazine (1,4-diazine), triazine, tetrazole, and oxadiazole (furazan).

Examples of $C_{5-20}$ heterocyclic groups (some of which are $C_{5-20}$ heteroaryl groups) which comprise fused rings, include, but are not limited to, $C_9$ heterocyclic groups derived from benzofuran, isobenzofuran, indole, isoindole, purine (e.g., adenine, guanine), benzothiophene, benzimidazole; $C_{10}$ heterocyclic groups derived from quinoline, isoquinoline, benzodiazine, pyridopyridine, quinoxaline; $C_{13}$ heterocyclic groups derived from carbazole, dibenzothiophene, dibenzofuran; $C_{14}$ heterocyclic groups derived from acridine, xanthene, phenoxathiin, phenazine, phenoxazine, phenothiazine.

The above $C_{1-7}$ alkyl, $C_{3-20}$ heterocyclyl, and $C_{5-20}$ aryl groups, whether alone or part of another substituent, may themselves optionally be substituted with one or more groups selected from themselves and the additional substituents listed below.

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.

$C_{1-7}$ alkoxy: —OR, wherein R is a $C_{1-7}$ alkyl group. Examples of $C_{1-7}$ alkoxy groups include, but are not limited to, —OCH$_3$ (methoxy), —OCH$_2$CH$_3$ (ethoxy) and —OC(CH$_3$)$_3$ (tert-butoxy).

Oxo (keto, -one): =O. Examples of cyclic compounds and/or groups having, as a substituent, an oxo group (=O) include, but are not limited to, carbocyclics such as cyclopentanone and cyclohexanone; heterocyclics, such as pyrone, pyrrolidone, pyrazolone, pyrazolinone, piperidone, piperidinedione, piperazinedione, and imidazolidone; cyclic anhydrides, including but not limited to maleic anhydride and succinic anhydride; cyclic carbonates, such as propylene carbonate; imides, including but not limited to, succinimide and maleimide; lactones (cyclic esters, —O—C(=O)— in a ring), including, but not limited to, β-propiolactone, γ-butyrolactone, δ-valerolactone, and ε-caprolactone; and lactams (cyclic amides, —NH—C(=O)— in a ring), including, but not limited to, β-propiolactam, γ-butyrolactam (2-pyrrolidone), δ-valerolactam, and ε-caprolactam.

Imino (imine): =NR, wherein R is an imino substituent, for example, hydrogen, $C_{1-7}$ alkyl group, a $C_{3-20}$ heterocyclyl group, or a $C_{5-20}$ aryl group, preferably hydrogen or a $C_{1-7}$ alkyl group. Examples of ester groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)CH₃ (acetyl), —C(=O)CH₂CH₃ (propionyl), —C(=O)C(CH₃)₃ (butyryl), and —C(=O)Ph (benzoyl, phenone).

Carboxy (carboxylic acid): —COOH.

Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)OCH₃, —C(=O)OCH₂CH₃, —C(=O)OC(CH₃)₃, and —C(=O)OPh.

Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —OC(=O)CH₃ (acetoxy), —OC(=O)CH₂CH₃, —OC(=O)C(CH₃)₃, —OC(=O)Ph, and —OC(=O)CH₂Ph.

Amido (carbamoyl, carbamyl, aminocarbonyl, carboxamide): —C(=O)NR¹R², wherein R¹ and R² are independently amino substituents, as defined for amino groups. Examples of amido groups include, but are not limited to, —C(=O)NH₂, —C(=O)NHCH₃, —C(=O)N(CH₃)₂, —C(=O)NHCH₂CH₃, and —C(=O)N(CH₂CH₃)₂, as well as amido groups in which R¹ and R², together with the nitrogen atom to which they are attached, form a heterocyclic structure as in, for example, piperidinocarbonyl, morpholinocarbonyl, thiomorpholinocarbonyl, and piperazinocarbonyl.

Acylamido (acylamino): —NR¹C(=O)R², wherein R¹ is an amide substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group, and R² is an acyl substituent, for example, a $C_{1-7}$ alkyl group, a $C_{3-20}$ heterocyclyl group, or a $C_{5-20}$ aryl group, preferably hydrogen or a $C_{1-7}$ alkyl group. Examples of acylamide groups include, but are not limited to, —NHC(=O)CH₃, —NHC(=O)CH₂CH₃, and —NHC(=O)Ph. R¹ and R² may together form a cyclic structure, as in, for example, succinimidyl, maleimidyl and phthalimidyl:

succinimidyl    maleimidyl    phthalimidyl

Acylureido: —N(R¹)C(O)NR²C(O)R³ wherein R¹ and R² are independently ureido substituents, for example, hydrogen, a $C_{1-7}$ alkyl group, a $C_{3-20}$ heterocyclyl group, or a $C_{5-20}$ aryl group, preferably hydrogen or a $C_{1-7}$ alkyl group. R³ is an acyl group as defined for acyl groups. Examples of acylureido groups include, but are not limited to, —NHCONHC(O)H, —NHCONMeC(O)H, —NHCONEtC(O)H, —NHCONMeC(O)H, —NHCONMeC(O)Me, —NHCONEtC(O)Et, —NMeCONHC(O)Et, —NMeCONHC(O)Me, —NMeCONHC(O)Et, —NMeCONMeC(O)Me, —NMeCONEtC(O)Et, and —NMeCONHC(O)Ph.

Carbamate: —NR¹—C(O)—OR² wherein R¹ is an amino substituent as defined for amino groups and R² is an ester group as defined for ester groups. Examples of carbamate groups include, but are not limited to, —NH—C(O)—O-Me, —NMe—C(O)—O-Me, —NH—C(O)—O-Et, —NMe—C(O)—O-t-butyl, and —NH—C(O)—O-Ph.

Thioamido (thiocarbamyl): —C(=S)NR¹R², wherein R¹ and R² are independently amino substituents, as defined for amino groups. Examples of amido groups include, but are not limited to, —C(=S)NH₂, —C(=S)NHCH₃, —C(=S)N(CH₃)₂, and —C(=S)NHCH₂CH₃.

Tetrazolyl: a five membered aromatic ring having four nitrogen atoms and one carbon atom, Amino: —NR¹R², wherein R¹ and R² are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$ alkyl group, or, in the case of a "cyclic" amino group, R¹ and R², taken together with the nitrogen atom to which they are attached, form a heterocyclic ring having from 4 to 8 ring atoms. Examples of amino groups include, but are not limited to, —NH₂, —NHCH₃, —NHC(CH₃)₂, —N(CH₃)₂, —N(CH₂CH₃)₂, and —NHPh. Examples of cyclic amino groups include, but are not limited to, aziridino, azetidino, pyrrolidino, piperidino, piperazino, morpholino, and thiomorpholino.

Imino: =NR, wherein R is an imino substituent, for example, for example, hydrogen, a $C_{1-7}$ alkyl group, a $C_{3-20}$ heterocyclyl group, or a $C_{5-20}$ aryl group, preferably H or a $C_{1-7}$ alkyl group.

Amidine: —C(=NR)NR₂, wherein each R is an amidine substituent, for example, hydrogen, a $C_{1-7}$ alkyl group, a $C_{3-20}$ heterocyclyl group, or a $C_{5-20}$ aryl group, preferably H or a $C_{1-7}$ alkyl group. An example of an amidine group is —C(=NH)NH₂.

Carbazoyl (hydrazinocarbonyl): —C(O)—NN—R¹ wherein R¹ is an amino substituent as defined for amino groups. Examples of azino groups include, but are not limited to, —C(O)—NN—H, —C(O)—NN-Me, —C(O)—NN-Et, —C(O)—NN-Ph, and —C(O)—NN—CH₂-Ph.

Nitro: —NO₂.

Nitroso: —NO.

Azido: —N₃.

Cyano (nitrile, carbonitrile): —CN.

Isocyano: —NC.

Cyanato: —OCN.

Isocyanato: —NCO.

Thiocyano (thiocyanato): —SCN.

Isothiocyano (isothiocyanato): —NCS.

Sulfhydryl (thiol, mercapto): —SH.

Thioether (sulfide): —SR, wherein R is a thioether substituent, for example, a $C_{1-7}$ alkyl group (also referred to as a $C_{1-7}$ alkylthio group), a $C_{3-20}$ heterocyclyl group, or a $C_{5-20}$ aryl group, preferably a $C_{1-7}$ alkyl group. Examples of $C_{1-7}$ alkylthio groups include, but are not limited to, —SCH₃ and —SCH₂CH₃.

Disulfide: —SS—R, wherein R is a disulfide substituent, for example, a $C_{1-7}$ alkyl group, a $C_{3-20}$ heterocyclyl group, or a $C_{5-20}$ aryl group, preferably a $C_{1-7}$ alkyl group (also referred to herein as $C_{1-7}$ alkyl disulfide). Examples of $C_{1-7}$ alkyl disulfide groups include, but are not limited to, —SSCH₃ and —SSCH₂CH₃.

Sulfone (sulfonyl): —S(=O)$_2$R, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group. Examples of sulfone groups include, but are not limited to, —S(=O)$_2$CH$_3$ (methanesulfonyl, mesyl), —S(=O)$_2$CF$_3$ (triflyl), —S(=O)$_2$CH$_2$CH$_3$, —S(=O)$_2$C$_4$F$_9$ (nonaflyl), —S(=O)$_2$CH$_2$CF$_3$ (tresyl), —S(=O)$_2$Ph (phenylsulfonyl), 4-methylphenylsulfonyl (tosyl), 4-bromophenylsulfonyl (brosyl), and 4-nitrophenyl (nosyl).

Sulfine (sulfinyl, sulfoxide): —S(=O)R, wherein R is a sulfine substituent, for example, a $C_{1-7}$ alkyl group, a $C_{3-20}$ heterocyclyl group, or a $C_{5-20}$ oaryl group, preferably a $C_{1-7}$ alkyl group. Examples of sulfine groups include, but are not limited to, —S(=O)CH$_3$ and —S(=O)CH$_2$CH$_3$. Sulfonyloxy: —OS(=O)$_2$R, wherein R is a sulfonyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfonyloxy groups include, but are not limited to, —OS(=O)$_2$CH$_3$ and —OS(=O)$_2$CH$_2$CH$_3$.

Sulfinyloxy: —OS(=O)R, wherein R is a sulfinyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfinyloxy groups include, but are not limited to, —OS(=O)CH$_3$ and —OS(=O)CH$_2$CH$_3$.

Sulfonamino: —NR$^1$S(=O)$_2$R, wherein R$^1$ is an amino substituent, as defined for amino groups, and R is a sulfonamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfonamino groups include, but are not limited to, —NHS(=O)$_2$CH$_3$ and —N(CH$_3$)S(=O)$_2$C$_6$H$_5$. A special class of sulfonamino groups are those derived from sultams—in these groups one of R$^1$ and R is a $C_{5-20}$ aryl group, preferably phenyl, whilst the other of R$^1$ and R is a bidentate group which links to the $C_{5-20}$ aryl group, such as a bidentate group derived from a $C_{1-7}$ alkyl group. Examples of such groups include, but are not limited to:

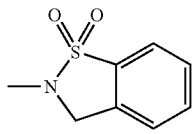

2,3-dihydro-benzo[d]isothiazole-1,1-dioxide-2-yl

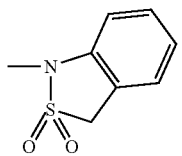

1,3-dihydro-benzo[c]isothiazole-2,2-dioxide-1-yl

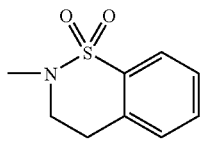

3,4-dihydro-2H-benzo[e][1,2]thiazine-1,1-dioxide-2-yl

Sulfinamino: —NR$^1$S(=O)R, wherein R$^1$ is an amino substituent, as defined for amino groups, and R is a sulfinamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfinamino groups include, but are not limited to, —NHS(=O)CH$_3$ and —N(CH$_3$)S(=O)C$_6$H$_5$.

Sulfamyl: —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido: —S(=O)$_2$NR$^1$R$^2$, wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

Phosphoramidite: —OP(OR$^1$)—NR$^2_2$, where R$^1$ and R$^2$ are phosphoramidite substituents, for example, —H, a (optionally substituted) $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphoramidite groups include, but are not limited to, —OP(OCH$_2$CH$_3$)—N(CH$_3$)$_2$, —OP(OCH$_2$CH$_3$)—N(i-Pr)$_2$, and —OP(OCH$_2$CH$_2$CN)—N(i-Pr)$_2$.

Phosphoramidate: —OP(=O)(OR$^1$)—NR$^2_2$, where R$^1$ and R$^2$ are phosphoramidate substituents, for example, —H, a (optionally substituted) $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphoramidate groups include, but are not limited to, —OP(=O)(OCH$_2$CH$_3$)—N(CH$_3$)$_2$, —OP(=O)(OCH$_2$CH$_3$)—N(i-Pr)$_2$, and —OP(=O)(OCH$_2$CH$_2$CN)—N(i-Pr)$_2$.

In many cases, substituents may themselves be substituted. For example, a $C_{1-7}$ alkoxy group may be substituted with, for example, a $C_{1-7}$ alkyl (also referred to as a $C_{1-7}$ alkyl-$C_{1-7}$alkoxy group), for example, cyclohexylmethoxy, a $C_{3-20}$ heterocyclyl group (also referred to as a $C_{5-20}$ aryl —$C_{1-7}$ alkoxy group), for example phthalimidoethoxy, or a $C_{5-20}$ aryl group (also referred to as a $C_{5-20}$aryl-$C_{1-7}$alkoxy group), for example, benzyloxy.

Includes Other Forms

Included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group.

Similarly, a reference to a hydroxyl group also includes the anionic form (—O$^-$), a salt or solvate thereof, as well as conventional protected forms of a hydroxyl group.

Isomers, Salts, Solvates, Protected Forms, and Prodrugs

Certain compounds may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r- forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., C$_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

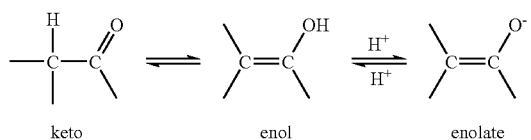

keto    enol    enolate

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including (wholly or partially) racemic and other mixtures thereof. Methods for the preparation (e.g. asymmetric synthesis) and separation (e.g., fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts", *J. Pharm. Sci.*, Vol. 66, pp. 1–19.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{3+}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulphuric, sulphurous, nitric, nitrous, phosphoric, and phosphorous. Examples of suitable organic anions include, but are not limited to, those derived from the following organic acids: acetic, propionic, succinic, glycolic, stearic, palmitic, lactic, malic, pamoic, tartaric, citric, gluconic, ascorbic, maleic, hydroxymaleic, phenylacetic, glutamic, aspartic, benzoic, cinnamic, pyruvic, salicyclic, sulfanilic, 2-acetyoxybenzoic, fumaric, phenylsulfonic, toluenesulfonic, methanesulfonic, ethanesulfonic, ethane disulfonic, oxalic, pantothenic, isethionic, valeric, lactobionic, and gluconic. Examples of suitable polymeric anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form", as used herein, pertains to a compound in which one or more reactive functional groups are protected from undesirable chemical reactions, that is, are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts, Wiley, 1999).

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH$_3$, —OAc).

For example, an aldehyde or ketone group may be protected as an acetal or ketal, respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide or a urethane, for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases, as an N-oxide (>NO$).

For example, a carboxylic acid group may be protected as an ester for example, as: an $C_{1-7}$ alkyl ester (e.g. a methyl ester; a t-butyl ester); a $C_{1-7}$ haloalkyl ester (e.g., a $C_{1-7}$ trihaloalkyl ester); a tri$C_{1-7}$ alkylsilyl-$C_{1-7}$ alkyl ester; or a $C_{5-20}$ aryl—$C_{1-7}$ alkyl ester (e.g. a benzyl ester; a nitrobenzyl ester); or as an amide, for example, as a methyl amide.

For example, a thiol group may be protected as a thioether (—SR), for example, as: a benzyl thioether; an acetamidomethyl ether (—S—$CH_2$NHC(=O)$CH_3$).

It may be convenient or desirable to prepare, purify, and/or handle the active compound in the form of a prodrug. The term "prodrug", as used herein, pertains to a compound which, when metabolised (e.g. in vivo), yields the desired active compound. Typically, the prodrug is inactive, or less active than the active compound, but may provide advantageous handling, administration, or metabolic properties.

For example, some prodrugs are esters of the active compound (e.g. a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required. Examples of such metabolically labile esters include those wherein R is $C_{1-7}$ alkyl (e.g. -Me, -Et); $C_{1-7}$ aminoalkyl (e.g. aminoethyl; 2-(N,N-diethylamino)ethyl; 2-(4-morpholino) ethyl); and acyloxy-$C_{1-7}$ alkyl (e.g. acyloxymethyl; acyloxyethyl; e.g. pivaloyloxymethyl; acetoxymethyl; 1-acetoxyethyl; 1-(1-methoxy-1-methyl)ethyl-carbonxyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy) carbonyloxymethyl; 1-(4-tetrahydropyranyloxy)carbonyloxyethyl; (4-tetrahydropyranyl)carbonyloxymethyl; and 1-(4-tetrahydropyranyl)carbonyloxyethyl).

Also, some prodrugs are activated enzymatically to yield the active compound, or a compound which, upon further chemical reaction, yields the active compound. For example, the prodrug may be a sugar derivative or other glycoside conjugate, or may be an amino acid ester derivative.

Selective Inhibition

'Selective inhibition' means the inhibition of one enzyme to a greater extent than the inhibition of one or more other enzymes. This selectivity is measurable by comparing the concentration of a compound required to inhibit 50% of the activity ($IC_{50}$) of one enzyme against the concentration of the same compound required to inhibit 50% of the activity ($IC_{50}$) of the other enzyme (see below). The result is expressed as a ratio. If the ratio is greater than 1, then the compound tested exhibits some selectivity in its inhibitory action.

The compounds of the present invention preferably exhibit a selectivity of greater than 5, 15 or 40 against DNA-PK over PI 3-kinase.

The compounds of the present invention preferably exhibit a selectivity of greater than 5, 10, 50 or 100 against DNA-PK over ATM.

The $IC_{50}$s used to determine selectivity are preferably determined using the methods described herein.

FURTHER PREFERENCES

Figure 1:
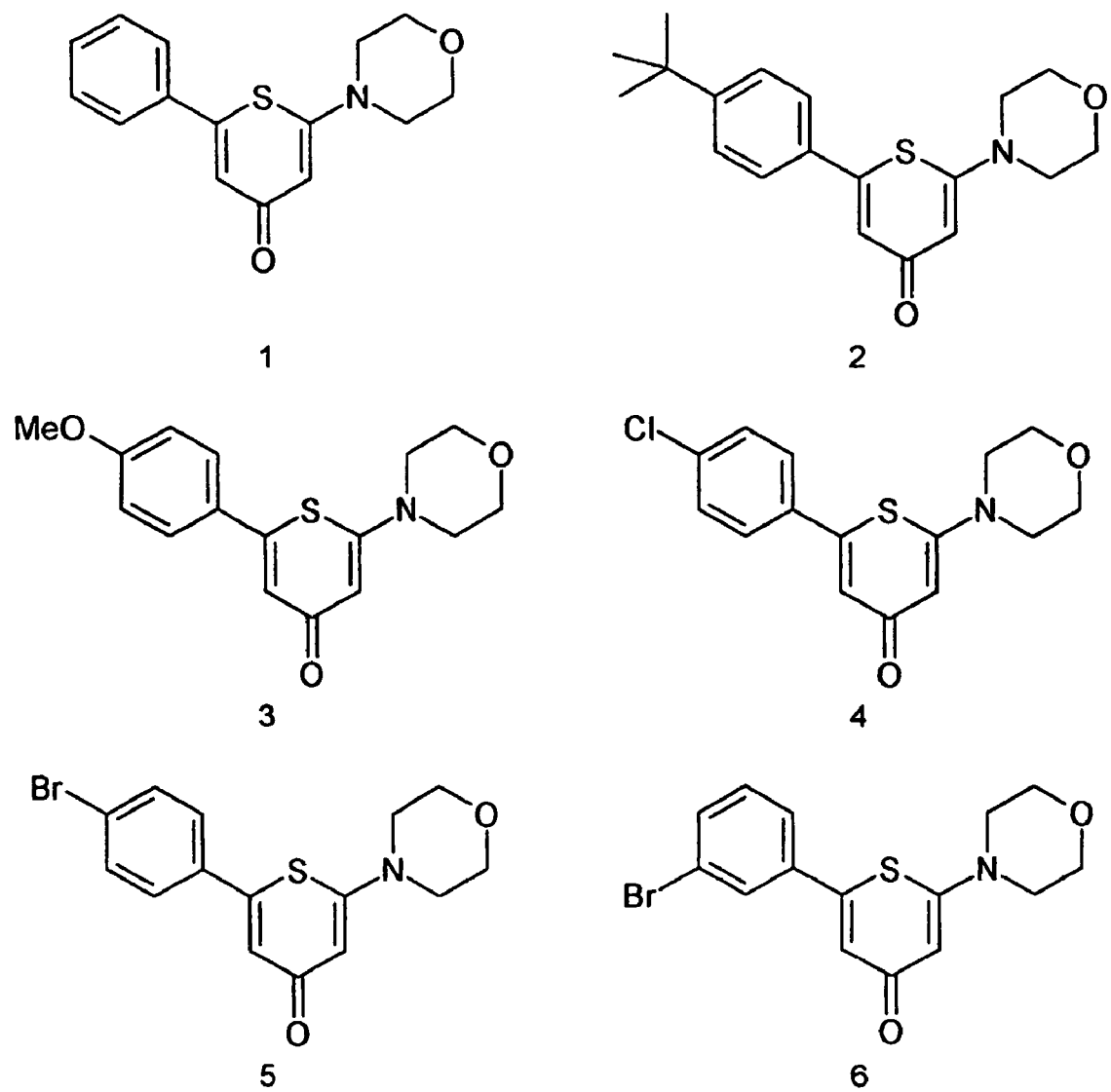
FIG. 1 shows the structure of selected compounds of formula I.

In formula I, when $R^1$ and $R^2$ form, along with the nitrogen atom to which they are attached, a heterocyclic ring having from 4 to 8 atoms, this may form part of a $C_{4-20}$ heterocyclyl group defined above (except with a minimum of 4 ring atoms), which must contain at least one nitrogen ring atom. It is preferred that $R^1$ and $R^2$ form, along with the nitrogen atom to which they are attached, a heterocyclic ring having 5, 6 or 7 atoms, more preferably 6 ring atoms.

Single rings having one nitrogen atom include azetidine, azetidine, pyrrolidine (tetrahydropyrrole), pyrroline (e.g., 3-pyrroline, 2,5-dihydropyrrole), 2H-pyrrole or 3H-pyrrole (isopyrrole, isoazole), piperidine, dihydropyridine, tetrahydropyridine, and azepine; two nitrogen atoms include imidazolidine, pyrazolidine (diazolidine), imidazoline, pyrazoline (dihydropyrazole), and piperazine; one nitrogen and one oxygen include tetrahydrooxazole, dihydrooxazole, tetrahydroisoxazole, dihydroisoxazole, morpholine, tetrahydrooxazine, dihydrooxazine, and oxazine; one nitrogen and one sulphur include thiazoline, thiazolidine, and thiomorpholine.

Preferred rings are those containing one heteroatom in addition to the nitrogen, and in particular, the preferred heteroatoms are oxygen and sulphur. Thus preferred groups include morpholino, thiomorpholino, thiazolinyl. Preferred groups without a further heteroatom include pyrrolidino.

The most preferred groups are morpholino and thiomorpholino.

As mentioned above, these heterocyclic groups may themselves be substituted; a preferred class of substituent is a $C_{1-7}$ alkyl group. When the heterocyclic group is morpholino, the substituent group or groups are preferably methyl or ethyl, and more preferably methyl. A sole methyl substituent is most preferably in the 2 position.

As well as the single ring groups listed above, rings with bridges or cross-links are also envisaged. Examples of these types of ring where the group contains a nitrogen and an oxygen atom are:

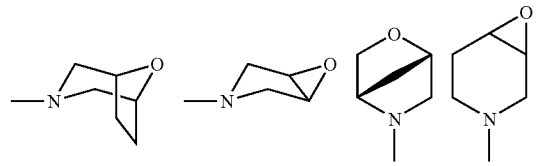

These are named 8-oxa-3-aza-bicyclo[3.2.1]oct-3-yl, 6-oxa-3-aza-bicyclo[3.1.0]hex-3-yl, 2-oxa-5-aza-bicyclo[2.2.1]hept-5-yl, and 7-oxa-3-aza-bicyclo[4.1.0]hept-3-yl, respectively.

$R^3$ is preferably a $C_{5-20}$ aryl group, more preferably a $C_{5-20}$ carboaryl group, and in particular an optionally substituted phenyl group. Preferred substituents include $C_{5-20}$ aryl, $C_{3-20}$ heterocyclyl (particularly morpholino), alkoxy (particularly methoxy), halo (particularly chloro or bromo) and $C_{1-7}$ alkyl (particularly t-butyl or phenyl substituted alkenyl, for example ethenyl). The $C_{5-20}$ aryl substituent may be $C_{5-20}$ carboaryl, and in particular phenyl or napthyl, or $C_{5-20}$ heteroaryl, and in particular heteroaryl containing one hetero ring atom.

If the substituent is a phenyl group it is preferably substituted, with the substituent being preferably selected from the group consisting of: hydroxy, halo (in particular, chloro), carboxy, amino (in particular $NH_2$), amido, formyl, cyano, $C_{5-20}$ aryl (in particular, phenyl), $C_{1-7}$ alkyl (in particular, methyl or ethenyl, and optionally further substituted, by, for example, hydroxy, $NH_2$, phenyl), acyl (where the acyl substituent is preferably $C_{1-7}$ alkyl, and more preferably methyl), acylamido (where the acyl substituent is preferably $C_{1-7}$ alkyl, and more preferably methyl), ester (where the ester substituent is preferably $C_{1-7}$ alkyl, and more preferably methyl, ethyl or trifluoromethyl) and ether (where the ether substituent is preferably $C_{1-7}$ alkyl, which may itself be further substituted, for example, by $C_{5-20}$ aryl, to give, e.g. benzyl).

It is generally preferred that the substituents are in the meta(3-) or para (4-) position with para (4-) being more preferred.

Examples of preferred compounds of this type include 2-(morpholin-4-yl)-6-phenyl-thiopyran-4-one (Compound 1), 2-(4-tert-Butyl-phenyl)-6-morpholin-4-yl-pyran-4-one (Compound 2), 2-(4-Methoxy-phenyl)-6-morpholin-4-yl-pyran-4-one (Compound 3) and 2-(4-Chloro-phenyl)-6-morpholin-4-yl-pyran-4-one (Compound 4).

Acronyms

For convenience, many chemical moieties are represented using well known abbreviations, including but not limited to, methyl (Me), ethyl (Et), n-propyl (nPr), iso-propyl (iPr), n-butyl (nBu), tert-butyl (tBu), n-hexyl (nHex), cyclohexyl (cHex), phenyl (Ph), biphenyl (biPh), benzyl (Bn), naphthyl (naph), methoxy (MeO), ethoxy (EtO), benzoyl (Bz), and acetyl (Ac).

For convenience, many chemical compounds are represented using well known abbreviations, including but not limited to, methanol (MeOH), ethanol (EtOH), iso-propanol (i-PrOH), methyl ethyl ketone (MEK), ether or diethyl ether ($Et_2O$), acetic acid (AcOH), dichloromethane (methylene chloride, DCM), trifluoroacetic acid (TFA), dimethylformamide (DMF), tetrahydrofuran (THF), and dimethylsulfoxide (DMSO).

Synthesis Routes

Compounds as described in the first aspect of the invention can be synthesised as described below, illustrated in respect of when $R^3$ is a phenyl group. The key step in this synthesis route is the formation of the central aromatic ring, accomplished by means of dithioic acid formation and subsequent condensative cyclisation.

If $R^3$ is desired not to be a phenyl ring, the appropriate $C_{3-20}$ heterocyclyl or $C_{5-20}$ aryl may be used in its place in the starting material. The required substitution on the aryl or heteroaryl group may be present in the starting material, as exemplified below, or may be introduced at any stage of the synthesis route, with the use of protecting groups as necessary. For example, if $R^x$ is a bromo group, further substitution can be added using Suzuki coupling of organoboron compounds.

2-amino-6-aryl-thiopyran-4-ones

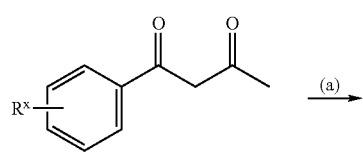

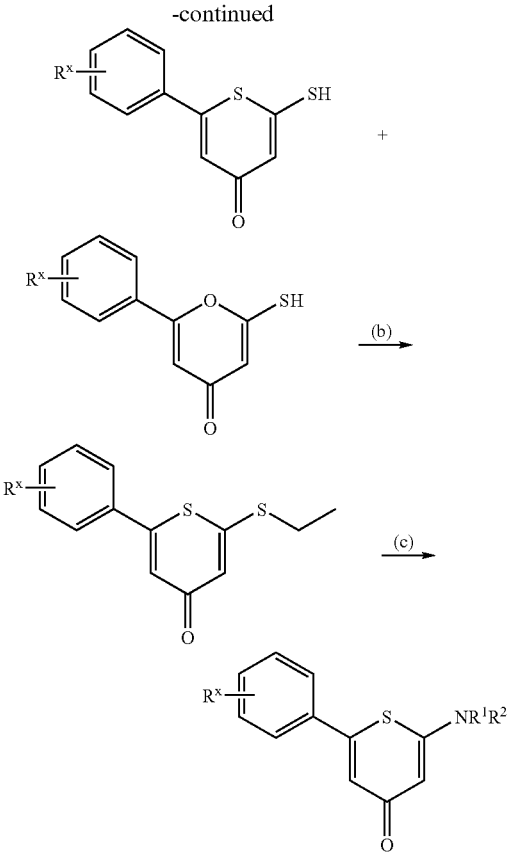

(a) LDA, $CS_2$, THF
(b) EtI, $K_2CO_3$, Acetone
(c) $R^1R^2NH$, ethylene glycol, 160° C.

(a) 2-mercapto-6-aryl-thiopyran-4-ones

Diisopropylamine (5.92 ml, 42 mmol) was dissolved in dry THF (20 ml) and was cooled to 0° C. under $N_2$. Butyl lithium (2.5 M in hexane, 16.8 ml, 42 mmol) was added dropwise to the stirred solution and was then left for 30 min. The solution of LDA was then cooled to −78° C. and 1-aryl-butane-1,3-dione (20 mmol) in dry THF (20 ml) was added dropwise to the solution. After two hours, $CS_2$ in dry THF (20 ml) was added dropwise to the solution at −78° C. and a red coloration was observed upon the $CS_2$ addition. The reaction mixture was left to warm up slowly to room temperature overnight and water (50 ml) was then added. The aqueous were acidified to pH 2–3 with 2N HCl at 0° C. (Watmann pH paper) and the organic were extracted with ether (3×100 ml), dried over $Na_2SO_4$ and evaporated in vacuo to give an orange oil which upon trituration with a petroleum ether/acetone 40/60 mix gave an orange solid.

This orange solid was found to be a mixture of 2-mercapto-6-aryl-thiopyran-4-one and 2-mercapto-6-aryl-pyran-4-one that was not possible to separate and was used without further purification.

(b) 2-Ethylsulfanyl-6-aryl-thiopyran-4-ones

2-Mercapto-6-aryl-thiopyran-4-one (6 mmol), finely powdered $K_2CO_3$ and iodoethane in dry acetone (20 ml) were refluxed for 4 h under vigorous stirring and a $N_2$ atmosphere. The solvent was then removed in vacuo and the residue taken into water (20 ml). The organic were extracted in ethyl acetate (3×30 ml), dried over $Na_2SO_4$ and evaporated in vacuo. The residue was purified by column chromatography (ethyl acetate/petroleum ether 40/60) to give the title compound.

(c) 2-amino-6-aryl-thiopyran-4-ones

2-Ethylsulfanyl-6-aryl-thiopyran-4-one (2 mmol) was dissolved in ethylene glycol (4 ml) and amine (4 ml) was added to the solution in one portion. The mixture was heated at 115° C. until the disappearance of the starting material (24 h), cooled to room temperature and then poured into water (50 ml). The organics were extracted with dichloromethane (3×30 ml), dried over $Na_2SO_4$ and the solvent evaporated in vacuo. The residue was purified by column chromatography (ethyl acetate/petroleum ether 40/60) to give the desired product.

Suzuki coupling where $R^x$ is Br

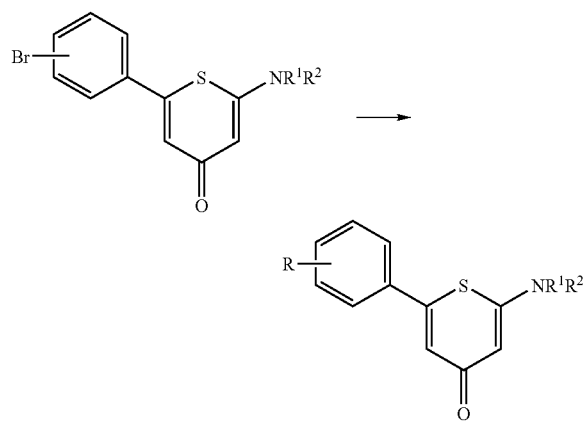

The appropriate organoboron compound (0.0625 mmol) and powdered potassium carbonate (19 mg, 0.14 mmol) were added to a reaction tube, which was then purged with nitrogen and sealed. Bromophenyl-2-morpholin-4-yl-thiopyran-4-one (e.g. compounds 5 or 6) (20 mg, 0.057 mmol) was dissolved in dioxane (1 mL) and the solution was degassed with nitrogen purge and sonication for 5 minutes before adding to the reaction tube. To this was added a solution of tetrakis(triphenylphosphine)palladium(0) (3 mg) in degassed dioxane (0.3 mL) and the reaction mixture was heated to 90° C. with stirring under a nitrogen atmosphere for 18 hours. The reaction was cooled and passed through a silica plug (isolute Si 500 mg cartridge) and eluted with 25% MeOH/$CH_2Cl_2$ (3 mL) The solution was purified by preparative HPLC.

Use of Compounds of the Invention

The present invention provides active compounds, specifically, active 2-amino-6-aryl-thiopyran-4-ones and 2-amino-6-heteroaryl-thiopyran-4-ones.

The term "active", as used herein, pertains to compounds which are capable of inhibiting DNA-PK activity, and specifically includes both compounds with intrinsic activity (drugs) as well as prodrugs of such compounds, which prodrugs may themselves exhibit little or no intrinsic activity.

One assay which may be used in order to assess the DNA-PK inhibition offered by a particular compound is described in the examples below.

The present invention further provides a method of inhibiting DNA-PK inhibition in a cell, comprising contacting said cell with an effective amount of an active compound, preferably in the form of a pharmaceutically acceptable composition. Such a method may be practised in vitro or in vivo.

For example, a sample of cells (e.g. from a tumour) may be grown in vitro and an active compound brought into contact with said cells in conjunction with agents that have a known curative effect, and the enhancement of the curative effect of the compound on those cells observed.

The present invention further provides active compounds which inhibit DNA-PK activity as well as methods of methods of inhibiting DNA-PK activity comprising contacting a cell with an effective amount of an active compound, whether in vitro or in vivo.

The invention further provides active compounds for use in a method of treatment of the human or animal body. Such a method may comprise administering to such a subject a therapeutically-effective amount of an active compound, preferably in the form of a pharmaceutical composition.

The term "treatment", as used herein in the context of treating a condition, pertains generally to treatment and therapy, whether of a human or an animal (e.g. in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e. prophylaxis) is also included.

The term "therapeutically-effective amount" as used herein, pertains to that amount of an active compound, or a material, composition or dosage from comprising an active compound, which is effective for producing some desired therapeutic effect, commensurate with a reasonable benefit/risk ratio.

Administration

The active compound or pharmaceutical composition comprising the active compound may be administered to a subject by any convenient route of administration, whether systemically/ peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly.

The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orang-utan, gibbon), or a human.

Formulations

While it is possible for the active compound to be administered alone, it is preferable to present it as a pharmaceutical composition (e.g. formulation) comprising at least one active compound, as defined above, together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilisers, or other materials, as described herein.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, excipients, etc. can be found in standard pharmaceutical texts, for example, *Remington's Pharmaceutical Sciences,* 18th edition, Mack Publishing Company, Easton, Pa., 1990.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, losenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g. by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or moulding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g. sodium lauryl sulfate); and preservatives (e.g. methyl p-hydroxybenzoate, propyl p-hydroxybenzoate, sorbic acid). Moulded tablets may be made by moulding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g. transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include losenges comprising the active compound in a flavoured basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose. Suitable formulations wherein the carrier is a liquid for administration as, for example, nasal spray, nasal drops, or by aerosol administration by nebuliser, include aqueous or oily solutions of the active compound.

Formulations suitable for administration by inhalation include those presented as an aerosol spray from a pressurised pack, with the use of a suitable propellant, such as dichlorodifluoromethane, trichlorofluoromethane, dichorotetrafluoroethane, carbon dioxide, or other suitable gases.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues. When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low.

Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required.

Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g. by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/ml to about 10 μg/ml, for example from about 10 ng/ml to about 1 μg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Dosage

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment.

Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 μg to about 250 mg per kilogram body weight of the subject per day. Where the active compound is a salt, an ester, prodrug, or the like, the amount administered is calculated on the basis of the parent compound and so the actual weight to be used is increased proportionately.

EXAMPLES

The following are examples are provided solely to illustrate the present invention and are not intended to limit the scope of the invention, as described herein.

Synthesis Details

Compound 1

(b) 2-Ethylsulfanyl-6-phenyl-thiopyran-4-one

From (4 g, 18.2 mmol) of 2-mercapto-6-phenyl-thiopyran-4-one gave a brown oil (3 g, 66%); FT-IR (ATR/cm$^{-1}$): 3055, 2970, 2931, 1588, 1335, 1246, 873, 691; $^1$H NMR (CDCl$_3$) δ=1.35 (3H, t); 3.04 (2H, q); 6.93 (1H, d); 7.02 (1H, d); 7.38–7.52 (5H, m); MS: m/z (LC-MS/ESP+): 249 (M$^+$+1)

(c) 2-Morpholin-4-yl-6-phenyl-thiopyran-4-one (1)

Dark orange needles (104 g, 19%); mp 160–161° C.; FT-IR (ATR/cm$^{-1}$): 3055, 2956, 2859, 1602, 1519, 1350, 1218, 864, 695; $^1$H NMR (DMSO) δ=3.42–3.55 (4H, t, J=4.5 Hz, CH$_2$N); 3.82 (4H, t, J=4.5 Hz, CH$_2$O); 6.17 (1H, s, H-3); 6.96 (1H, s, H-5); 7.62–7.64 (3H, m, ArH); 7.77–7.81 (2H, m, ArH); UV: λ$_{max}$ (MeOH): 301, 258.5; MS: m/z (LC-MS/ESP+): 274 (M$^+$+1); Calcd C$_{15}$H$_{15}$NO$_2$S: C 65.91; H, 5.53; N, 5.12; Found: C, 65.72; H, 5.57; N, 5.12.

Compound 2

(b) 2-(4-tert-butyl-phenyl)-6-ethylsulfanyl-thiopyran-4-one White solid (1.01 g, 55%); mp 98–99° C.; FT-IR (ATR/cm$^{-1}$): 3046, 2947, 2863, 1596, 1517, 1334, 1257, 979, 840; $^1$H NMR (CDCl$_3$) λ=1.28 (9H, s), 1.35 (3H, t), 3.03 (2H, q), 6.89 (1H, d), 7.00 (1H, d), 7.43 (4H, s); MS: m/z (LC-MS/ESP+): 305 (M$^+$+1);

(c) 2-(4-tert-Butyl-phenyl)-6-morpholin-4-yl-thiopyran-4-one (2)

White crystalline plate (160 mg, 24%); mp 172–173° C.; FT-IR (ATR/cm$^{-1}$): 2962, 2844, 1604, 1570, 1527, 1440, 1356, 1210, 1119, 1069, 868, 831, 808; $^1$H NMR (CDCl$_3$) δ=1.32 (9H, s, (CH$_3$)$_3$), 3.40 (3H, t, J=5 Hz, CH$_2$N), 3.81 (3H, t, J 5 Hz, CH$_2$O), 6.14 (1H, bs, H-3), 6.92 (1H, bs, H-5), 7.47 (4H, m, ArH); UV: λ (MeOH/nm)=301.5, 263.5 (λ$_{max}$); m/z (LC-MS/ESP): 330(M$^+$+1).

Compound 3

(b) 2-(4-methoxy-phenyl)-6-ethylsulfanyl-thiopyran-4-one

From (4 g, 16 mmol) of 2-mercapto-6-(4-methoxy-phenyl)-thiopyran-4-one gave an orange solid (2.84 g, 64%);

mp 61–62° C.; FT-IR (ATR/cm$^{-1}$): 3047, 3008, 2962, 2931, 1597, 1504, 1257, 1180, 1017, 824; $^1$H NMR (CDCl$_3$) δ=1.34 (3H, t), 3.02 (2H, q), 6.87–6.95 (5H, m), 7.44 (2H, d); MS: m/z (LC-MS/ESP+): 279 (M$^+$+1)

(c) 2-(4-Methoxy-phenyl)-6-morpholin-4-yl-thiopyran-4-one (3)

White solid (184 mg, 30%); mp 199–200° C.; FT-IR (ATR/cm$^{-1}$): 2937, 2839, 1603, 1531, 1506, 1354, 1255, 1209, 1178, 1116, 817, $^1$H NMR (CDCl$_3$) δ=3.34 (3H, t, J 5 Hz, CH$_2$N), 3.76 (3H, t, J 5 Hz, CH$_2$O), 6.07 (1H, d, J 1 Hz, H-3), 6.82 (1H, d, J 1 Hz, H-5), 6.89 (2H, d, J 8 Hz, ArH), 7.44 (2H, d, J=8 Hz, ArH); UV: λ(MeOH/nm)=338, 301, 261 (λ$_{max}$), 223; MS: m/z (LC-MS/ESP): 304 (M$^+$+1).

Compound 4

(b) 2-(4-Chloro-phenyl)-6-ethylsulfanyl-thiopyran-4-one

From (1.27 g, 5 mmol) of 2-mercapto-6-(4-chloro-phenyl)-thiopyran-4-one gave a white solid (0.66 g, 47%); mp 90–91° C.; FT-IR (ATR/cm$^{-1}$): 3090, 3016, 2962, 2931, 1597, 1519, 1481, 1327, 979, 887, 817; $^1$H NMR (CDCl$_3$) δ=1.42 (3H, t), 3.32 (2H, q), 7.05 (1H, d), 7.21 (1H, d), 7.70 (2H, d), 7.85 (2H, d); MS: m/z (LC-MS/ESP+): 283 (M$^+$+1);

(c) 2-(4—Chloro-phenyl)-6-morpholin-4-yl-thiopyran-4-one (4)

White solid (210 mg, 34%); mp 202–204° C.; FT-IR (ATR/cm$^{-1}$): 3058, 2966, 2870, 1595, 1550, 1525, 1350, 1216, 1113, 1092, 1028, 880, 812; $^1$H NMR (CDCl$_3$) δ=3.39 (3H, t, J 5 Hz, CH$_2$N), 3.81 (3H, t, J 5 Hz, CH$_2$O), 6.13 (1H, d, J 1 Hz, H-3), 6.89 (1H, d, J 1 Hz, H-5), 7.38–7.49 (4H, m, ArH); UV: λ (nm/MeOH)=307, 263 (λ$_{max}$); MS: m/z (LC-MS/ESP+): 308–310(M$^+$+1).

Compound 5

1-(4-Bromophenyl)-butane-1,3-dione

To a suspension of sodium ethoxide (4.49 g, 66 mmol) in EtOAc (10 mL) that was cooled to −5° C. was added a solution of 4-bromoacetophenone (11.94 g, 60 mmol) in EtOAc (10 mL) and THF (10 mL). The mixture was stirred at 0° C. for 4 hours before warming to ambient temperature and stirring for 48 hours. Water (20 mL) and dichloromethane (40 mL) were added and a white precipitate was filtered from the mixture. To the solid was added 2N HCl, with vigorous stirring, to pH 1. EtOAc (100 mL) was added and separated, and the water was washed with EtOAc (2×100 mL). The organic portions were combined, dried (Na$_2$SO$_4$) and concentrated in vacuo to yield the desired compound as a pale yellow, crystalline solid (11.09 g, 76%); $^1$H-NMR (CDCl$_3$): 2.13 (s, 3H, CH$_3$), 6.07 (s, 1H, =CH), 7.52 (d, 2H, J=8.7 Hz, Ar-2, Ar-6), 7.67 (d, 2H, J=8.7 Hz, Ar-3, Ar-5).

(a) 6- (4-Bromophenyl)-2-mercapto-thiopyran-4-one

To a stirred solution of LDA (20 mL, 40 mmol) in 40 mL anhydrous THF under an atmosphere of nitrogen was added slowly a solution of 1-(4-Bromophenyl)-butane-1,3-dione (4.84 g, 20 mmol) dissolved in THF (30 mL). After addition was complete the mixture was allowed to warm slowly to ambient temperature and stir for 10 minutes. The solution was re-cooled to −78° C. for the addition of a solution of carbon disulfide (1.2 mL, 20 mmol) in THF (20 mL). This temperature was maintained for 2 hours, before warm warmed slowly to ambient temperature and stirred for 18 hours. Cold water (150 mL) was added and mixture was heated to 60° C. with good stirring for 3 hours. The volatiles were removed in vacuo and the aqueous solution was washed with diethyl ether (2×100 mL). The aqueous solution was acidified to pH 1 with 2N HCl, and the orange precipitate was filtered from the acid, washed with water, and dried by vacuum desiccation. Orange solid (5.07 g, 85%); LCMS m/z 299, 301 ([M+1]$^+$) 298, 300 ([M−1]$^-$), $^1$H-NMR (D$_6$-DMSO): 7.10 (s, 1H, H-3), 7.36 (s, 1H, H-5), 7.69 (d, 2H, J=8.6 Hz, Arom), 7.76 (d, 2H, J=8.6 Hz, Arom); infrared spectrum (cm$^{-1}$): 815, 950, 1008, 1072, 1202, 1451, 1364, 1451, 1487, 1508, 1584.

(b) 6-(4-Bromophenyl)-2-ethylsulfanyl-thiopyran-4-one

Brown solid (1.45 g, 98%); LCMS m/z 327, 329 ([M+1]$^+$).

(c) 6-(4-Broinophenyl)-2-morpholin-4-yl-thiopyran-4-one (5)

Beige solid (3.43 g, 42%); m.p. 214–215° C.; R$_f$=0.52 (10% MeOH/DCM); LCMS m/z 352, 354 ([M+1]$^+$); $^1$H-NMR (CDCl$_3$): 3.34–3.37 (4H, m, 2×NCH$_2$), 3.75–3.78 (4H, m, 2×OCH$_2$), 6.10 (s, 1H, H-3), 6.85 (s, 1H, H-5), 7.36 (d, 2H, J=8.6 Hz, Arom), 7.53 (d, 2H, J=8.6 Hz, Arom); infrared spectrum (cm$^{-1}$): 804, 879, 1034, 1113, 1216, 1349, 1489, 1527, 1596, 2870, 2967, 3281; UV spectrum λ$_{max}$=264 nm.

Compound 6

1-(3-Bromophenyl)-butane-1,3-dione

To a suspension of sodium ethoxide (3.82 g, 55 mmol) in EtOAc (10 mL) that was cooled to −5° C. was added a solution of 3-bromoacetophenone (10.0 g, 50 mmol) in EtOac (10 mL) and THF (10 mL). The mixture was stirred at 0° C. for 4 hours before warming to ambient temperature and stirring for 48 hours. Water (20 mL) and dichloromethane (40 mL) were added. The aqueous layer was separated, and acidified to pH 1 by addition of 2N HCl. EtOAc (100 mL) was added and separated, and the water was washed with EtOAc (2×100 mL). The organic portions were combined, dried (Na$_2$SO$_4$) and concentrated in vacuo to yield title compound as a beige, waxy solid (9.57 g, 79%).

(a) 6- (3-Bromophenyl) -2-mercapto-thiopyran-4-one

To a stirred solution of LDA (20 mL, 40 mmol) in 40 mL anhydrous THF under an atmosphere of nitrogen was added slowly a solution of 1-(3-Bromophenyl)-butane-1,3-dione (4.84 g, 20 mmol) dissolved in THF (30 mL). After addition was complete the mixture was allowed to warm slowly to ambient temperature and stir for 10 minutes. The solution was re-cooled to −78° C. for the addition of a solution of carbon disulfide (1.2 mL, 20 mmol) in THF (20 mL). This temperature was maintained for 2 hours, before warm warmed slowly to ambient temperature and stirred for 18 hours. Cold water (150 mL) was added and mixture was heated to 60° C. with good stirring for 3 hours. The volatiles were removed in vacuo and the aqueous solution was washed with diethyl ether (2×100 mL). The aqueous solution was acidified to pH 1 with 2N HCl, and the orange precipitate was filtered from the acid, washed with water, and dried by vacuum desiccation. Orange solid (4.28 g, 72%); m.p. 188° C. (decomp); LCMS m/z 299, 301 ([M+1]$^+$) 298, 300 ([M−1]$^-$), 1H-NMR (D$_6$-DMSO): 7.07 (d, 1H, J=1.4 Hz, H-3), 7.36 (d, 1H, J=1.4 Hz, H-5), 7.47–7.52 (dd, 1H, J1=J2=7.9 Hz, Ar-5), 7.69–7.72 (d, 1H, J=7.9 Hz, Ar-4/6), 7.76–7.78 (d, 1H, J=7.9 Hz, Ar-4/6), 7.92 (s, 1H, Ar-2); infrared spectrum (cm$^{-1}$): 815, 950, 1008, 1072, 1202, 1451, 1364, 1451, 1487, 1508, 1584.

(b) 6-(3-Bromophenyl)-2-ethylsulfanyl-thiopyran-4-one

Brown solid (4.34 g, 93%); LCMS m/z 327, 329 ([M+1]$^+$).

(c) 6-(3-Bromophenyl)-2-morpholin-4-yl-thiopyran-4-one (6)

Beige solid (1.44 g, 37%); m.p. 181–182° C.; $R_f$=0.47 (10% MeOH/DCM); LCMS m/z 352, 354 ([M+1]$^+$); $^1$H-NMR (CDCl$_3$): 3.34–3.38 (4H, m, 2×NCH$_2$), 3.76–3.79 (4H, m, 2×OCH$_2$), 6.10 (s, 1H, H-3), 6.86 (s, 1H, H-5), 7.24–7.30 (dd, 1H, J1=J2=7.9 Hz, Ar-5), 7.41–7.44 (d, 1H, J=7.9 Hz, Ar-4/6), 7.52–7.56 (d, 1H, J=7.9 Hz, Ar-4/6), 7.64 (s, 1H, Ar-2); infrared spectrum (cm$^{-1}$): 856, 875, 1034, 1111, 1215, 1347, 1531, 1578, 1618, 2875, 2961; UV spectrum $\lambda_{max}$=252 nm.

Compounds Synthesised by Suzuki Coupling from Compound 5, where the organoboron compound was a substituted phenyl compound

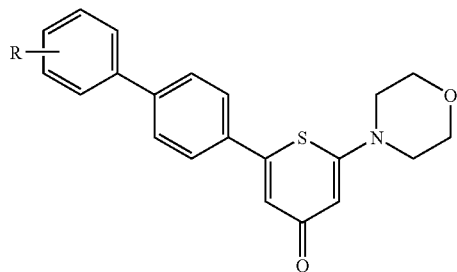

| Compound | Substituent position | Substituent | LCMS [M+]$^+$ | Purity |
|---|---|---|---|---|
| 7 | 2 | *—O—CH$_2$—C$_6$H$_5$ | 456 | 85 |
| 8 | 3 | *—CH=CH—C(O)—O—CH$_3$ | 434 | 85 |
| 9 | 4 | *—C(O)—O—CH$_3$ | 408 | 90 |
| 10 | 3 | *—NH—C(O)—CH$_3$ | 407 | 85 |
| 11 | 3 | *—C(O)—CH$_3$ | 392 | 90 |
| 12 | 3 | *—C(O)—O—CH$_2$CH$_3$ | 422 | 90 |
| 13 | 3 | *—CH$_2$OH | 380 | 85 |
| 14 | 3 | *—OH | 366 | 90 |
| 15 | 3 | *—NH$_2$ | 365 | 90 |
| 16 | 2 | *—C(O)—NH$_2$ | 393 | 90 |
| 17 | 4 | *—NH—C(O)—CH$_3$ | 407 | 85 | from Compound 6, where the organoboron compound was a substiuted phenyl compound

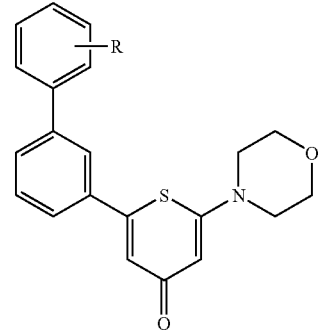

| Compound | Substituent position | Substituent | LCMS [M+]$^+$ | Purity |
|---|---|---|---|---|
| 18 | 2 | *—O—CH$_2$—C$_6$H$_5$ | 456 | 85 |
| 19 | 3 | *—O—CH$_2$—C$_6$H$_5$ | 456 | 90 |
| 20 | 4 | *—C≡N | 375 | 90 |
| 21 | 2 | *—CH=CH—C(O)—O—CH$_3$ | 434 | 90 |
| 22 | 3 | *—CH=CH—C(O)—O—CH$_3$ | 434 | 90 |

-continued
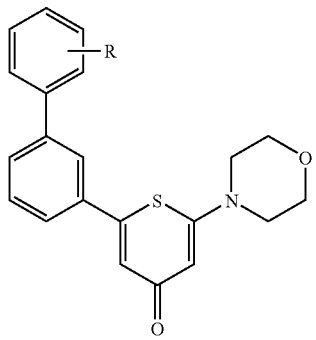
| Compound | Substituent position | Substituent | LCMS [M+]+ | Purity |
|---|---|---|---|---|
| 23 | 2 |  | 408 | 90 |
| 24 | 4 |  | 408 | 90 |
| 25 | 3 | 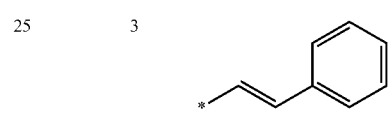 | 376 | 90 |
| 26 | 3 | 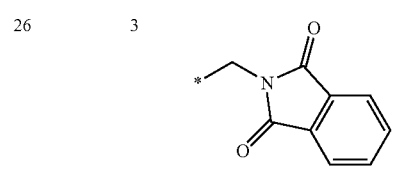 | 509 | 85 |
| 27 | 4 | 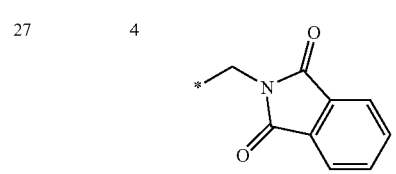 | 509 | 90 |
| 28 | 2 |  | 392 | 85 |
| 29 | 4 |  | 380 | 90 |
| 30 | 2 |  | 426 | 90 |
| 31 | 3 |  | 407 | 85 |
| 32 | 4 |  | 426 | 90 |
-continued
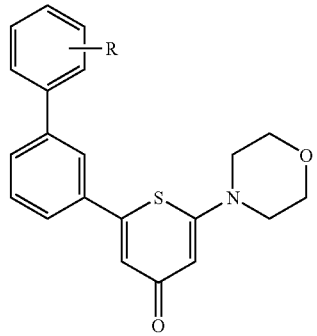
| Compound | Substituent position | Substituent | LCMS [M+]+ | Purity |
|---|---|---|---|---|
| 33 | 3 | 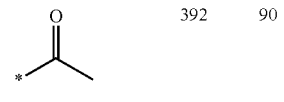 | 392 | 90 |
| 34 | 3 |  | 434 | 90 |
| 35 | 3 |  | 426 | 90 |
| 36 | 3 |  | 408 | 90 |
| 37 | 2 |  | 378 | 90 |
| 38 | 4 | *—Cl | 384 | 90 |
| 39 | 2 |  OH | 384 | 85 |
| 40 | 3 |  OH | 380 | 90 |
| 41 | 4 |  OH | 380 | 90 |
| 42 | 3 | *—OH | 366 | 85 |
| 43 | 4 | *—OH | 366 | 90 |
| 44 | 3 |  | 394 | 85 |
| 45 | 4 | 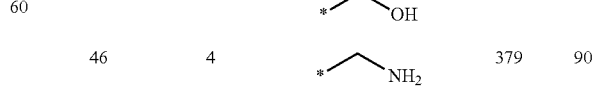 | 394 | 90 |
| 46 | 4 |  NH2 | 379 | 90 |
| 47 | 2 | *—NH2 | 365 | 85 |

-continued

[Structure: biphenyl-substituted thiopyranone with morpholine, R on terminal phenyl ring]

| Compound | Substituent position | Substituent | LCMS [M+]+ | Purity |
|---|---|---|---|---|
| 48 | 4 | *—NH₂ | 365 | 90 |
| 49 | 3 | *—NH₂ | 365 | 90 |
| 50 | 4 | *—NH—C(=O)—CH₃ | 407 | 90 |
| 51 | 2 | *—NH—C(=O)—CH₃ | 407 | 90 |
| 52 | 3 | *—C(=O)—O—ethyl | | |
| 53 | 3 | *—NH₂ | 408 | 90 |
| | 3' | *—C(=O)—OH | | | from Compound 5

[Structure: 4-R-phenyl thiopyranone with morpholine]

| Compound | Substituent | LCMS[M+]+ | Purity |
|---|---|---|---|
| 54 | 1,4-naphthyl (attached at 1, * at 4) | 414 | 90 |
| 55 | styryl (phenyl-CH=CH-*) | 376 | 85 |
| 56 | benzothiophen-3-yl | 406 | 90 |
| 57 | thiophen-2-yl | 356 | 85 |
| 58 | furan-2-yl | 340 | 90 |
| 59 | naphth-1-yl | 400 | 90 |
| 60 | 3-formylthiophen-2-yl | 384 | 85 |
| 61 | 4-formylnaphth-1-yl | 428 | 90 |

-continued

[Structure: 4-position R-substituted phenyl, 6-morpholino, thiopyran-4-one]

| Compound | Substituent | LCMS[M+]+ | Purity |
|---|---|---|---|
| 62 | morpholine (N-linked) | 359 | 90 | from Compound 6

[Structure: 3-position R-substituted phenyl, 6-morpholino, thiopyran-4-one]

| Compound | Substituent | LCMS[M+]+ | Purity |
|---|---|---|---|
| 63 | 4-methylnaphthalen-1-yl | 414 | 90 |
| 64 | benzo[b]thiophen-3-yl | 406 | 90 |
| 65 | thiophen-3-yl | 356 | 90 |
| 66 | naphthalen-2-yl | 400 | 90 |

-continued

[Structure: 3-position R-substituted phenyl, 6-morpholino, thiopyran-4-one]

| Compound | Substituent | LCMS[M+]+ | Purity |
|---|---|---|---|
| 67 | furan-2-yl | 340 | 90 |
| 68 | benzo[b]thiophen-2-yl | 406 | 85 |
| 69 | naphthalen-1-yl | 400 | 90 |
| 70 | 3-formylthiophen-2-yl | 384 | 90 |
| 71 | 4-formylnaphthalen-1-yl | 428 | 90 |
| 72 | quinolin-8-yl | 401 | 90 |

BIOLOGICAL EXAMPLES

DNA-PK Inhibition

In order to assess the inhibitory action of the compounds against DNA-PK in vitro, the following assay was used.

Mammalian DNA-PK, isolated from Hela cell nuclear extract (Gell, D. and Jackson S. P., *Nucleic Acids Res.* 27:3494–3502 (1999)), was incubated with Z buffer (25 mM Hepes (Sigma); 12.5 mM $MgCl_2$ (Sigma); 50 mM KCl (Sigma); 1 mM DTT (Sigma); 10% Glycerol (Sigma); 0.1% NP-40 (Sigma); pH 7.4) in polypropylene 96 well plates and varying concentrations of inhibitor added. All compounds were diluted in DMSO to give a final assay concentration of between 10 and 0.01 µM, with DMSO being at a final concentration of 1% per well. The total assay volume per well was 40 µl.

After 10 minutes of incubation at 30° C. the reactions were initiated by the addition of Na-ATP (50 µM final), $^{33}$P-γATP and a 30mer double stranded DNA oligonucleotide (10 ng/µl) in a volume of 10 µl. Designated positive and negative reaction wells were done in combination with compound wells (unknowns) in order to calculate % enzyme activities. The plates were then shaken for 2 minutes and incubated at 30° C. for 45 minutes.

Following the incubation, the reactions were quenched by the addition of 50 µl 30% acetic acid to each well. The plates were then shaken for 5 minutes and the contents of each plate (80 µl from each well) transferred over to a 96 well Polyfiltronics filtration plate, containing P81-phosphocellulose membrane (TRADE MARK)(Whatman, UK). The solutions were vacuum pumped through the membrane and each well membrane washed four times using 300 µl of 15% acetic acid. The well membranes were then air dried and 20 µl of scintillant was added to each well.

The plates were transferred to a TopCount NXT (TRADE MARK) (Packard, UK) for scintillation counting. Values recorded are counts per minute (cpm) following a 1 minute counting time for each well.

The enzyme activity for each compound is then calculated using the following equation:

$$\% \text{ Inhibition} = 100 - \left( \frac{(cpm \text{ of unknown} - \text{mean negative } cpm) \times 100)}{(\text{mean positive } cpm - \text{mean negative } cpm)} \right)$$

In Table 1 below, the results are IC$_{50}$ values (the concentration at which 50% of the enzyme activity is inhibited). These are determined over a range of different concentrations, normally from 10 µM down to 0.01 µM. Such IC$_{50}$ values are used as comparative values to identify increased compound potencies. LY294002 exhibited an IC$_{50}$ of 1.5 µM. For many of the compounds synthesised, the inhibition was measured at a single concentration, for example, 1 µm.

Enhancement Ratio

The Enhancement Ratio (ER) is a ratio of the enhancement of cell growth inhibition elicited by the DNA-PK inhibitor after 2 Grays of irradiation compared to untreated control cells. DNA-PK inhibitors were used at a fixed concentration of 25 micromolar. Radiation was delivered by a Faxitron 43855D X-ray system at a dose rate of lGy per minute The Enhancement ratio at 2 Gy irradiation was calculated from the formula:

$$ER = \frac{\text{Cell growth in presence of } DNA-PK \text{ inhibitor} \times \text{Cell growth after } IR}{\text{Cell growth of untreated cells} \times \text{Cell growth after } IR \text{ in presence of } DNA-PK \text{ inhibitor}}$$

Cell growth was assessed using the sulforhodamine B (SRB) assay (Skehan, P., Storung, R., Scudiero, R., Monks, A., McMahon, J., Vistica, D., Warren, J. T., Bokesch, H., Kenny, S. and Boyd, M. R. (1990) New colorimetric cytotoxicity assay for anticancer-drug screening. J. Natl. Cancer Inst. 82:1107–1112). 400 HeLa cells were seeded into each well of a flat-bottomed 48-well microtiter plate in a volume of 200 µl and incubated for 6 h at 37° C. Cells were either replaced with media alone or with media containing DNA-PK inhibitor at a final concentration of 25 µM. Cells were allowed to grow for a further 1 h before irradiation or mock irradiation. Cells untreated with DNA-PK inhibitor or unirradiated were used as a control. Cells treated with DNA-PK inhibitor alone were used to assess the growth inhibition by the DNA-PK inhibitor.

Cells were left for a further 16 h before replacing the media and allowing the cells to grow for a further 6 days at 37° C. The media was then removed and the cells fixed with 200 µl of ice cold 10% (w/v) trichloroacetic acid. The plates were incubated at 4° C. for 20 minutes and then washed four times with water. Each well of cells was then stained with 200 µl of 0.4% (w/v) SRB in 1% acetic acid for 20 minutes before washing four times with 1% acetic acid. Plates were then dried for 2 h at room temperature. The dye from the stained cells was solubilized by the addition of 100 µl of 10 mM Tris Base into each well. Plates were gently shaken and left at room temperature for 30 minutes before measuring the optical density at 564 nM on a Microquant microtiter plate reader.

The results are detailed below in table 2. LY294002 exhibited an Enhancement Ration of 1.09.

PI 3-kinase Inhibition

In order to assess the inhibitory action of the compounds against PI 3-kinase in vitro, the following assay was used to determine IC$_{50}$ values.

Baculoviral recombinant GST-fused PI 3-kinase (p110α/p85α) was purified from Sf9 insect cells using GSH-sepharose affinity chromatography as described (Wymann, M. T et al., (1996) Wortmannin inactivates phosphoinositide 3-kinase by covalent modification of Lys-802, a residue involved in the phosphate transfer reaction. Mol. Cell Biol. 16:1722–1733). PI 3-kinase (1 µl) was diluted in reaction buffer (89 µl of 50 mM Hepes pH 7.5, 150 mM NaCl, 0.1 mM Sodium Orthovanadate, containing 20 µg of phosphatidylinositol) and varying concentrations of inhibitor compound added. All compounds were diluted in DMSO to give a final assay concentration of beween 100 and 0.1 µM, with DMSO being at a final concentration of 1%. After 10 minutes of incubation at 37° C. the reactions were initiated by the addition of 10 µl of 50 µM Na-ATP, 20 mM MgCl$_2$ and 2.5 µCi $^{33}$p-γATP. Reactions were incubated for a further 20 minutes at 37° C., before quenching with the addition of 400 µl of chloroform/methanol (1:1). Reactions were acidified by the addition of 200 µl of 1M HCl, before separation of the organic and aqueous phases by centrifugation at 10,000 g for 30 seconds. The organic phase was transferred to a fresh tube and washed twice with 150 µl of 1M hydrochloric acid/methanol (1:1), discarding the aqueous phase. The washed reaction product was then placed in a white 96-well plate with 100 µl of scintillation fluid and transferred to a TopCount NXT for scintillation counting. Counts per minute, following a one minute counting time, were recorded for each reaction. The inhibition of PI 3-kinase activity by compounds was calculated as described above for the DNA-PK assay.

The selectivity was determined by the following equation:

$$\Delta(DNA-PK/PI3-K) = \frac{IC_{50}(PI3-K)}{IC_{50}(DNA-PK)}$$

The results are detailed below in table 3. LY294002 exhibited an IC$_{50}$ of 1.5 μM, and a Δ(DNA-PK/PI 3-K) of 1.

ATM Inhibition

In order to assess the inhibitory action of the compounds against ATM in vitro, the following assay was used to determine IC$_{50}$ values.

ATM protein was immunoprecipitated from HeLa cell nuclear extract using rabbit polyclonal antisera raised to the C-terminal ~500 amino-acid residues of the human ATM protein. The immunoprecipitation was performed according to the methodology described by Banin, S. et al. (1998) Enhanced phosphorylation of p53 by ATM in response to DNA damage. Science 281:1674–1677. 10 μl of immunoprecipitated ATM in Buffer C (50 mM Hepes, pH 7.4, 6 mM MgCl2, 150 mM NaCl, 0.1 mM sodium orthovanadate, 4 mM MnCl2, 0.1 mM dithiothreitol, 10% glycerol) was added to 32.5 μl of buffer C containing 1 μg of the ATM substrate GSTp53N66 in a V-bottomed 96 well polypropylene plate. The GSTp53N66 substrate is the amino terminal 66 amino acid residues of human wild type p53 fused to glutathione S-transferase. ATM phosphorylates p53 on the residue serine 15 (Banin, S. et al. (1998) Enhanced phosphorylation of p53 by ATM in response to DNA damage. Science 281:1674–1677). Varying concentrations of inhibitor were then added. All compounds were diluted in DMSO to give a final assay concentration of beween 100 and 1 μM, with DMSO being at a final concentration of 1%. After 10 minutes of incubation at 37° C., the reactions were initiated by the addition of 5 μl of 50 μM Na-ATP. After 1 h with shaking at 37° C., 150 μl of phosphate buffered saline (PBS) was added to the reaction and the plate centrifuged at 1500 rpm for 10 minutes. 5 μl of the reaction was then transferred to a 96 well opaque white plate containing 45 μl of PBS to allow the GSTp53N66 substrate to bind to the plate wells. The plate was covered and incubated at room temperature for 1 h with shaking before discarding the contents. The plate wells were washed twice by the addition of PBS prior to the addition of 3% (w/v) bovine serum albumin (BSA) in PBS. The plate was incubated at room temperature for 1 h with shaking before discarding the contents and washing twice with PBS. To the wells, 50 μl of a 1:10, 000 dilution of primary phosphoserine-15 antibody (Cell Signaling Technology, #9284L) in 3% BSA/PBS was added to detect the phosphorylation event on the serine 15 residue of p53 elicited by the ATM kinase. After 1 h of incubation at room temperature with shaking, the wells were washed four times with PBS prior to the addition of an anti-rabbit HRP conjugated secondary antibody (Pierce, 31462) with shaking for 1 h at room temperature. The wells were then washed four times with PBS before the addition of chemiluminescence reagent (NEN Renaissance, NEL105). The plate was then shaken briefly, covered with a transparent plate seal and transferred to a TopCount NXT for chemiluminescent counting. Counts per second, following a one second counting time, were recorded for each reaction. The inhibition of ATM activity by compounds was calculated as described above for the DNA-PK assay.

The selectivity was determined by the following equation:

$$\Delta(DNA-PK/ATM) = \frac{IC_{50}(ATM)}{IC_{50}(DNA-PK)}$$

The results are detailed below in table 4. LY294002 exhibited an IC$_{50}$ of >100 μM, and a α(DNA-PK/ATM) of >67.

Results

TABLE 1

| DNA-PK Inhibition | |
| --- | --- |
| Compound Number | IC$_{50}$ (μM) |
| 1 | 0.6 |
| 2 | 0.8 |
| 3 | 0.4 |
| 4 | 0.7 |
| 5 | 0.7 |
| 6 | 1.8 |

Compounds 7 to 72 all exhibited at least 10% inhibition at 1 μM, with the following compounds exhibiting at least 50% inhibition at 2 μM (i.e. having an IC$_{50}$ of 2 μM or less): 14, 30, 31, 33, 35, 40, 41, 42, 43, 46, 48, 49, 51, 57, 59, 63, 64, 69, 70.

TABLE 2

| Enhancement Ratio | |
| --- | --- |
| Compound Number | ER |
| 1 | 1.58 |
| 3 | 1.51 |
| 4 | 2.26 |

TABLE 3

| PI 3-kinase Inhibition | | |
| --- | --- | --- |
| Compound Number | IC$_{50}$ (μM) | Δ (DNA-PK/PI 3-K) |
| 1 | 10 | 17 |
| 2 | 40 | 50 |
| 3 | 8 | 20 |
| 4 | 5 | 7 |

TABLE 4

| ATM Inhibition | | |
| --- | --- | --- |
| Compound Number | IC$_{50}$ (μM) | Δ (DNA-PK/ATM) |
| 1 | >100 | >167 |
| 2 | >100 | >125 |
| 3 | >100 | >250 |
| 4 | >100 | >143 |

What is claimed is:

1. A compound of formula I:

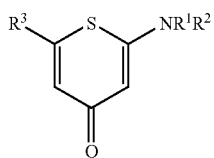

and isomers, salts, solvates, chemically protected forms, and prodrugs thereof, wherein:

$R^1$ and $R^2$ are independently hydrogen, an optionally substituted $C_{1-7}$ alkyl group, $C_{3-20}$ heterocyclyl group, or $C_{5-20}$ aryl group, or may together form, along with the nitrogen atom to which they are attached, an optionally substituted heterocyclic ring having from 4 to 8 ring atoms; and $R^3$ is an optionally substituted $C_{5-20}$ aryl group.

2. A compound according to claim 1, wherein $R^1$ and $R^2$ form, along with the nitrogen atom to which they are attached, a heterocyclic ring having 5, 6 or 7 ring atoms.

3. A compound according to claim 2, wherein the heterocyclic ring formed by $R^1$, $R^2$ and the nitrogen atom to which they are attached, has 6 ring atoms.

4. A compound according to claim 2, wherein said heterocyclic ring contains one further ring heteroatom in addition to the nitrogen atom.

5. A compound according to claim 1, wherein $R^3$ is a $C_{5-20}$ carboaryl group.

6. A compound according to claim 5, wherein $R_3$ is a phenyl group with one or more substituents selected from hydroxy, halo, carboxy, amino, amido, formyl, cyano, $C_{5-20}$ aryl, $C_{1-7}$ alkyl, acyl, acylamido, ester and ether.

7. A composition comprising a compound according to claim 1 and a pharmaceutically acceptable carrier or diluent.

8. A method for the treatment of tumours comprising administering to a subject suffering from tumour growth a therapeutically-effective amount of a compound according to claim 1 in combination with ionising radiation or one or more chemotherapeutic agents.

* * * * *